US012760063B2

(12) United States Patent
Daubert et al.

(10) Patent No.: US 12,760,063 B2
(45) Date of Patent: Oct. 13, 2026

(54) ELUATE COLLECTION DURING ANTIBODY CHROMATOGRAPHY

(71) Applicant: MORPHOSYS GMBH, Nürmberg (DE)

(72) Inventors: Daniela Daubert, Olching (DE); Dominik Geltinger, Landshut (DE); Karin Felderer, Munich (DE)

(73) Assignee: MorphoSys GmbH, Planegg (DE)

( * ) Notice: Subject to any disclaimer, the term of this patent is extended or adjusted under 35 U.S.C. 154(b) by 1119 days.

(21) Appl. No.: 17/777,366

(22) PCT Filed: Nov. 20, 2020

(86) PCT No.: PCT/EP2020/082804

§ 371 (c)(1),
(2) Date: May 17, 2022

(87) PCT Pub. No.: WO2021/099528

PCT Pub. Date: May 27, 2021

(65) Prior Publication Data

US 2022/0411465 A1 Dec. 29, 2022

(30) Foreign Application Priority Data

Nov. 22, 2019 (EP) ..................................... 19210867

(51) Int. Cl.
*C07K 1/16* (2006.01)
*C07K 1/18* (2006.01)
*C07K 16/24* (2006.01)

(52) U.S. Cl.
CPC .............. *C07K 1/18* (2013.01); *C07K 16/244* (2013.01)

(58) Field of Classification Search
None
See application file for complete search history.

(56) References Cited

U.S. PATENT DOCUMENTS 9,556,258 B2 1/2017 Nti-Gyabaah et al. ...................... C07K 16/18
2009/0318674 A1 12/2009 Gagnon ........................ 530/416
2013/0303732 A1 11/2013 Hewig, III et al. ........ 530/387.1
2016/0264618 A1 9/2016 Lee et al. .................. C07L 1/18
2016/0272673 A1 9/2016 Althouse et al. ...... C07K 1/165

FOREIGN PATENT DOCUMENTS

| | | |
|---|---|---|
| CN | 108699143 | 10/2018 |
| JP | 2011-522055 | 7/2011 |
| JP | 2014-520814 | 8/2014 |
| WO | 2009/149067 | 12/2009 |
| WO | 2013/009526 | 1/2013 |
| WO | 2014/140570 | 9/2014 |
| WO | 2016/096896 | 6/2016 |
| WO | 2017/140831 | 8/2017 |
| WO | 2019/057982 | 3/2019 |
| WO | 2019/171267 A1 | 9/2019 |

OTHER PUBLICATIONS

International Search Report and Written Opinion in PCT/EP2020/082804 dated Feb. 11, 2021.
International Preliminary Report on Patentability in PCT/EP2020/082804 dated May 17, 2022.
Extended European Search Report in EP Application No. 19210867.8 dated May 19, 2020.
Borg et al. "Modeling and robust pooling design of a preparative cation-exchange chromatography step for purification of monoclonal antibody monomer from aggregates" Journal of Chromatography A 2014 1359:170-181.
Westerberg et al. "Pooling control in variable preparative chromatography processes" Bioprocess Biosyst Eng 2010 33:375-382.
Yigsaw et al. "Ion Exchange Chromatography of Proteins and Clearance of Aggregates" Current Pharmaceutical Biotechnology 2009 10:421-426.
Khanal et al. "Multi-col. displacement chromatography for separation of charge variants of monoclonal antibodies" Journal of Chromatography A 2019 1586:40-51.
Nikolin et al. "High Performance Liquid Chromatography in Pharmaceutical Analysis" Bosnian Journal of Basic Medical Sciences 2004 4(2):5-9.
Office Action dated May 6, 2026 in U.S. Appl. No. 19/363,223, filed Oct. 20, 2025.

*Primary Examiner* — Michael D Pak
(74) *Attorney, Agent, or Firm* — Licata & Tyrrell P.C.

(57) ABSTRACT

The present invention relates to an improved method for peak fractionation and eluate collection during chromatography for purification of a human therapeutic antibody.

11 Claims, 16 Drawing Sheets

Specification includes a Sequence Listing.

| Fraction | Peak Frac. [mAU] | Yield [%] | HMW [%] | Monomer [%] | LMW [%] |
|---|---|---|---|---|---|
| Frac. 2.A.5 | 450 – 1000 | 3.2 | 3.7 | 90.6 | 5.6 |
| Frac. 2.B.5 | 1000 – 1400 | 5.4 | 1.8 | 96.2 | 2.0 |
| Frac. 2.C.5 | 1400 – 1523 | 5.1 | 1.2 | 97.7 | 1.1 |
| Pool | 1523 – 400 | 72.5 | 0.7 | 99.2 | 0.1 |

| Fraction | Peak Frac. [mAU] | Yield [%] | HMW [%] | Monomer [%] | LMW [%] |
|---|---|---|---|---|---|
| Frac. 2.A.3 | 450 – 1400 | 2.5 | 8.4 | 83.3 | 8.3 |
| Frac. 2.B.3 | 1400 – 1860 | 4.6 | 3.2 | 93.4 | 3.4 |
| Frac. 2.C.3 | 1860 – 1971 | 3.2 | 2.0 | 96.0 | 2.0 |
| Pool | 1971 – 400 | 81.6 | 0.8 | 99.0 | 0.2 |

Run #6

| Fraction | Peak Frac. [mAU] | Yield [%] | HMW [%] | Monomer [%] | LMW [%] |
|---|---|---|---|---|---|
| Frac. 2.C.5 | 900 ~ 1960 | 6.4 | 2.4 | 95.1 | 2.4 |
| Frac. 2.A.1 | 1960 ~ 2225 | 9.4 | 1.4 | 97.7 | 0.9 |
| Pool | 2225 ~ 400 | 71.3 | 0.6 | 99.2 | 0.1 |
| Frac. 2.C.1 | 400 ~ 300 | 1.5 | 0.6 | 99.2 | 0.1 |

| Fraction | Peak Frac. [mAU] | Yield [%] | HMW [%] | Monomer [%] | LMW [%] |
|---|---|---|---|---|---|
| Frac. 1.C.4 | 2550 – 2887 | 8.1 | 2.6 | 95.2 | 2.2 |
| Pool | 2887 – 400 | 76.8 | 0.8 | 99.0 | 0.2 |
| Frac. 1.C.5 | 400 – 300 | 1.0 | 1.0 | 98.8 | 0.2 |
| Frac. 2.A.1 | 300 – 220 | 0.7 | 1.3 | 98.5 | 0.2 |

| Fraction | Peak Frac. [mAU] | Yield [%] | HMW [%] | Monomer [%] | LMW [%] |
|---|---|---|---|---|---|
| Frac. 2.B.2 | 1680 - 1942 | 8.2 | 1.3 | 97.7 | 0.9 |
| Pool | 1942 - 400 | 74.6 | 0.6 | 99.2 | 0.2 |
| Frac. 2.A.3 | 400 - 300 | 1.6 | 0.7 | 99.2 | 0.1 |
| Frac. 2.B.3 | 300 - 240 | 1.2 | 0.8 | 99.1 | 0.1 |

| Fraction | Peak Frac. [mAU] | Yield [%] | HMW [%] | Monomer [%] | LMW [%] |
|---|---|---|---|---|---|
| Frac. 2.A.1 | 2470 – 2548 | 4.5 | 2.8 | 95.7 | 1.5 |
| Pool | 2548 – 400 | 78.8 | 0.7 | 99.0 | 0.3 |
| Frac. 2.B.1 | 400 – 300 | 1.0 | 0.8 | 99.1 | 0.1 |
| Frac. 2.C.1 | 300 – 240 | 0.7 | 1.0 | 98.9 | 0.1 |

| Fraction | Peak Frac. [mAU] | Yield [%] | HMW [%] | Monomer [%] | LMW [%] |
|---|---|---|---|---|---|
| Frac. 2.B.1 | 1900 – 2344 | 7.2 | 1.9 | 96.5 | 1.6 |
| Pool | 2344 – 400 | 76.1 | 0.6 | 99.2 | 0.2 |
| Frac. 2.A.2 | 400 – 300 | 1.2 | 0.7 | 99.1 | 0.2 |
| Frac. 2.B.2 | 300 – 230 | 0.9 | 0.9 | 98.9 | 0.2 |

$$\bar{x} = \frac{1}{n}\sum_{i=1}^{n}(C1 - C0) + (C2 - C0) + \cdots + (CN - C0)$$

$$D0 = \bar{x}$$

$$CX = C0 + D0$$

ELUATE COLLECTION DURING ANTIBODY CHROMATOGRAPHY

This patent application is the National Stage of International Application No. PCT/EP2020/082804 filed Nov. 20, 2020, which claims the benefit of priority from EP 19210867.8 filed Nov. 22, 2019, teachings of each of which are incorporated herein by reference in their entirety.

FIELD OF THE INVENTION

The present disclosure relates to a method for protein purification. In particular, the invention relates to an improved method for peak fractionation during antibody elution from a chromatography resin by using an optimized peak cut for starting collection of the eluate. This optimized peak cut can be applied consistently robust for starting eluate collections in elution runs with different elution peak widths and heights. More specifically, the invention relates to a method for purifying a human therapeutic antibody applying the improved peak cut for starting eluate collection during CEX polishing, and to a purified antibody composition, obtained by the method disclosed herein.

BACKGROUND OF THE INVENTION

For therapeutic administration, every pharmaceutical substance has to meet distinct quality criteria. To ensure clinical safety and tolerability e.g. of a therapeutic monoclonal antibody (mAb), one or more purification steps have to follow the manufacturing process of the mAb, e.g. to remove undesired contaminants such as aggregated and fragmented product, nucleic acids, viruses, host cell proteins (HCPs), residual media components, and cell culture additives. The goal of every manufacturing and purification process development is therefore to establish a reliable, reproducible and robust method that results in a protein product of high purity and yield. Importantly, maintaining consistent quality of the product from batch-to-batch is an absolute necessity in pharmaceutical production.

To achieve adequate homogeneity and to fulfill the high quality standards of therapeutic grade products to be used in clinical applications, so called polishing steps are a necessity in the stream of the purification process. Often these polishing steps include ion exchange chromatography (IEX) which is used after initial antibody affinity chromatography to remove residual aggregates and impurities.

Besides the choice of resin type and conditions to be applied during polishing (e.g. load density, bind-elute mode or flow-through mode), the selection of the fractionation mode (FIG. 1) is another important aspect. ‘Peak fractionation’ is the most efficient mode of eluate collection and can be used to increase the purity of the collected protein. For this, appropriate peak fractionation specifications for starting and terminating eluate collection during elution have to be determined. Peak fractionation ensures that the collected fraction of interest contains only a minimal amount of the substances eluting in the neighboring fractions (which are not collected). Peak fractionation may be performed manually or automatically. In the manual mode, the operator decides the change to the next fraction collection tube. In the automated fractionation mode, defined integration parameters (e.g. absorbance) control fractionation. Automated peak fractionation is only recommended if sample composition does not change between chromatographic runs because changes in sample composition (e.g. pH, salt concentration, conductivity, protein concentration, load density) may result in differing peak shapes, which may not be recognized by the integration parameters entered.

In industrial scale manufacturing, the peak cut parameters are typically a specific signal for absorbance at 280 nm (A280), conductivity or pH and are pre-defined as threshold for starting and stopping collecting fractions. For example, Borg et al. (J Chromatogr A. 2014 Sep. 12; 1359:170-81) disclose a pooling design that applies a constant start collection criterion that is triggered when the optical density (OD) at 280 nm reaches 0.5 during peak ascension. The end cut point is determined by a percentage of the maximum peak value. WO2014140570 relates to controlling collection of eluate output from a separation process with starting and stopping collection when a defined measure of the suspended material reaches a distinct threshold value. Yigzaw et al. (Curr Pharm Biotechnol. 2009 June; 10(4):421-6) describe the stopping of eluate collection based on absorbance variation at different % of peak maxima as the end cut point. Westerberg et al. (Bioprocess Biosyst Eng. 2010 March; 33(3):375-82) disclose a HIC case study in which a model simulation to determine the parameter that has the greatest influence on the choice of the first cut point to start collection was used. In this case, the parameter was determined to be the conductivity of the load buffer. Then a function was set to estimate the dependence of the absorption signal at the cut point on the conductivity of the sample load. The maximum of this function at a certain conductivity was then determined to be the ideal cut point.

US20160272673 describes chromatographic methods for isolating and purifying DVD-Igs™ from a sample, wherein the purified DVD-Igs™ have reduced host cell proteins, aggregates, and viruses compared to the sample. US20160264618 discloses a method for the purification of an antibody by cation exchange chromatography. There, eluate starts to be collected when the UV signal in a chromatogram increases to a predetermined value of 50 mAU, 100 mAU or higher depending on the elution run.

In general, the fractionation problem lies in the determination of optimal peak cut points for starting and ending eluate collection, such that product recovery is maximal and impurity concentrations absent or low and within the specification. Determining optimized peak collection criteria (for pooling the product eluate) that are less sensitive to sample composition and batch-to-batch disturbances of various process parameters (e.g. pH, load) is of great importance for scale-independent methods for purifying antibody proteins. In particular, purification methods resulting in compositions with an improved yield, high purity, and at the same time at reduced costs are of great value for process development.

US20130303732 provides a method for controlling contaminants in biopharmaceutical purification processes by using light scattering and UV absorbance as a continuous monitoring system to provide information about the elution peak fractions in real-time instead of conventional pooling methods that rely on a predetermined percent UV peak max value to initiate the pooling process irrespective of product quality The technical problem underlying the present application may be seen in the provision of means for improved antibody elution during chromatography with efficient reduction of aggregates and impurities by maintaining at the same time optimal yield of the target antibody independent of pH of the elution buffer, salt concentration and load density. The invention fulfils these needs by providing a method for specifying a reference absorbance signal that is used together with a predetermined flow volume interval to find out an optimized start-point for collection of the eluate. The advantage is that an ideal eluate collection start is realized, independent of often unpredictable peak heights and shapes of elution runs with different conditions. Furthermore, a method for peak fractionation by applying these improved peak start criteria during purification of a therapeutic antibody is provided.

SUMMARY OF THE INVENTION

Herein, the inventors provide a method for the purification of a protein by chromatography, comprising the following steps:

a) loading a sample comprising a protein onto a chromatography resin,
b) optionally, washing the resin,
c) applying an elution buffer to the chromatography resin, and
d) starting collection of the eluate, wherein the collection of the eluate is started at a predetermined interval (D0) after the absorbance signal of the eluate has reached a predetermined value (A0).

The determination of the absorbance signal A0, which is used as reference signal to obtain the starting signal for collecting the eluate at a predetermined interval D0 after A0 is reached, comprises the steps of a) receiving elution peak chromatograms of at least two different elution runs ($ER_1, \ldots, ER_N$) (N=integer greater than 1) with the protein sample to be purified, wherein the different elution runs vary in pH, load density or salt conditions, and
b) specifying an absorbance value A0 in the elution peaks, wherein A0 is in the range of 10-50% of the absorbance signal at peak maximum of each elution peak ($A_{MAX}1, \ldots, A_{MAX}N$), and the same between each elution peak of $ER_1, \ldots, ER_N$.

The predetermined interval D0 is a flow volume interval that is obtained by a method comprising the steps of:

a) receiving the elution peak chromatograms of at least two different elution runs ($ER_1, \ldots, ER_N$) with the protein sample to be purified, wherein the different elution runs vary in pH, load density or salt conditions,
b) specifying an absorbance signal $A_1, \ldots, A_N$ for each of the elution peaks received in step a), wherein each of the corresponding eluate fractions of $A_1, \ldots, A_N$ has an aggregate/impurity content below 5%,
c) determining the flow volumes $C_1, \ldots, C_N$ of the absorbance signals $A_1, \ldots, A_N$ for each of the elution runs in the chromatograms,
d) calculating the differences $D_1, \ldots, D_N$ for each of said flow volumes $C_1, \ldots, C_N$ to the flow volume of A0 (which is C0), and
e) averaging said differences $D_1, \ldots, D_N$ (i.e. obtaining the mean value), thereby obtaining the predetermined flow volume interval D0.

Furthermore, the inventors provide a method for purifying an antibody comprising applying a mixture containing an antibody and aggregates/impurities on to an ion exchange chromatography resin, washing the resin, eluting the antibody from the chromatography resin, and collecting eluate fractions by peak fractionation with a start-point for collection that is determined with the method described herein. The start of eluate collection is robust with regard to different peak widths and heights.

The method is in particular suited for purification of antibody samples delineated by chromatographic peaks with aggregate/impurity accumulation at the front (i.e. in the ascending part) of the peak. For example, as in the case with high molecular weight (HMW) and low molecular weight (LMW) impurities enriched at the beginning of a steeply increasing peak of an unpolished antibody sample as shown in FIG. 2.

Instead of defining a distinct A280 absorbance signal (absorbance measured at UV 280 nm) for starting eluate collection, the inventors have determined an A280 absorbance signal (indicated herein as A0) pointing to the onset of the peak. A0 is e.g. the same at the corresponding flow volume (measurement unit: column volume, CV) between normalized elution peaks of the at least two different elution runs, wherein the different elution runs vary in pH, salt or load density conditions. Alternatively, A0 is 50% of the absorbance signal of the peak maximum of the elution peak with the lowest height of the elution peaks of the different elution runs $E_1, \ldots, E_N$. Preferably, A0 is between 10% and 50% of all peak maxima of the elution peaks of the different elution runs $E_1, \ldots, E_N$.

The absorbance signal A0 intersects with the elution peak curves of the different elution runs $E1, \ldots, E_N$ at a flow volume C0 (measurement unit: column volume, CV). C0 might differ between the individual elution peaks of the different elution runs $E_1, \ldots, E_N$, depending on the shape of each of the elution peaks. The flow volume of A0, which is C0, is then to be used with a predetermined flow volume interval (termed 'delay' herein, e.g. 0.6 column volumes) at which a subsequent A280 absorbance signal is reached that together with its corresponding flow volume defines the starting point for eluate collection.

In one embodiment, the ion exchange chromatography step is a multimodal cation exchange chromatography step (Capto MMC ImpRes, GE Healthcare) in bind-elute mode, wherein the antibody is eluted from the column using a salt gradient.

In one embodiment, the antibody to be purified is a monoclonal antibody. The invention also provides a monoclonal antibody purified by a process that separated the monoclonal antibody from aggregates and/or impurities in a process stream using the method of this disclosure.

DETAILED DESCRIPTION OF THE INVENTION

Protein Purification by Chromatography

Figure 1:
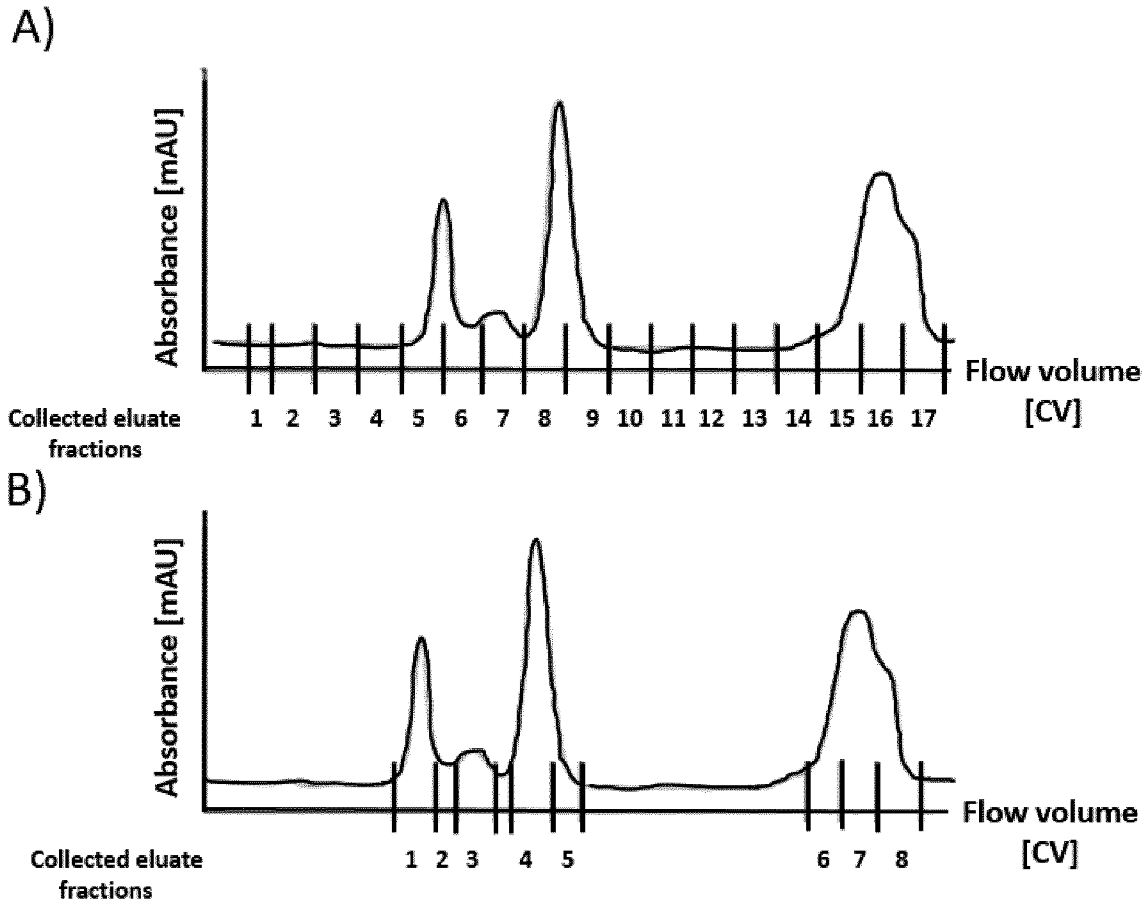
FIG. 1. Schematic chromatograms of fractionation modes using (A) fixed volume fractionation and (B) peak fractionation (modified from ÄKTA avant User Manual 29-0351-84 AD, GE Healthcare).

In the pharmaceutical industry, the manufacturing process for a target molecule, such as a therapeutic mAb, is typically divided into i) upstream processing (USP), including production of the target protein; ii) downstream processing (DSP), comprising yield of the target protein in a pure form by purification; and iii) final processing to gain product integrity and safety.

Typically, the first step of a downstream purification process, following the production phase, involves clarification of the harvested cell culture broth where one or more of steps of precipitation, flocculation, (depth) filtration and/or centrifugation are used to separate the desired protein from cells, cellular debris, and other contaminants. Downstream purification processes further typically include one or more (orthogonal) chromatographic separation steps such as affinity chromatography, ion-exchange, hydrophobic interaction, hydroxyapatite, chromatofocusing, gel filtration and reverse phase to efficiently remove process and product related impurities. These contaminants include but are not limited to host cell proteins (HCPs), leached protein A, product isoforms, high molecular weight (HMW) species, low molecular weight (LMW) species, and clipped or degraded product. Parameters that can led to HMW species such as dimers and larger order aggregates (multimers) include, but are not limited to protein concentration, pH, ionic strength, oxygen, temperature, salt concentration, shear forces, exposure to external stresses (such as the interaction with metal surfaces, exposure to air, freezing and/or thawing). Undesirable post-translational modifications or molecular unfolding can also promote aggregation.

Affinity chromatography refers to the use of a compound that specifically interacts with a desired target protein to be purified. Usually, the compound is immobilized on a resin for the purpose of isolating, purifying, or removing the desired target product. For example, for the purification of antibodies, affinity resins include Protein A obtained from *Staphylococcus aureus*, Protein G from *Streptococcus* sp., Protein L from *Peptostreptococcus magnus*, and recombinant or synthetic versions or peptides of such. The resins include MAbSelect™ (GE Healthcare), Prosep A® (Millipore) and others. For laboratory scale applications, a one-step affinity purification generally achieves satisfactory purity. Protein A chromatography, for example, as the most widely used affinity purification to capture antibodies supports purity of >95% with excellent recovery due to its high specificity to the Fc part of IgGs. Other examples of purification methods include thiophilic adsorption, hydrophobic interaction or aromatic adsorption chromatography, metal chelate affinity chromatography, and size exclusion chromatography (Vijayalakshmi, M. A., Appl. Biochem. Biotech. 75 (1998) 93-102). Further removal of residual aggregates and/or impurities can be achieved by a combination of one or two additional chromatographic steps that may include hydroxyapatite, hydrophobic interaction (HIC), and ion exchange chromatography (IEX, e.g. cation exchange (CEX), anion exchange (AEX), or mixed-mode exchange). At manufacturing scale, removal of aggregates and/or impurities is often achieved through use of ion exchange chromatography (IEX) after initial antibody affinity chromatography. Commercial multimodal ion exchangers such as Capto MMC and Capto adhere, as well as Capto MMC ImpRes and Capto adhere ImpRes (all from GE Healthcare) can be used for removal of contaminants downstream of the initial affinity capture. IEX separates proteins with differences in surface charge to give a high-resolution separation with high sample loading capacity. The separation is based on reversible electrostatic interactions between a charged protein (i.e. charged amino acid side chains) and an oppositely charged chromatography medium. AEX involves purification of proteins on a resin with positively charged functional groups (e.g. strong anion exchangers with quaternary amine group, or weak anion exchanger with secondary amine group). At pH values higher than the isoelectric point (pI) of the target protein, the net charge of the protein is negative, favoring its binding to a positively charged resin. Target protein elution is performed either with an increasing salt gradient, by step elution with a pre-defined pH and salt concentration or by decreasing elution buffer pH. CEX, on the other hand, involves purification of proteins on a resin with negatively charged functional groups (e.g. strong cation exchangers with sulfite groups, or weak cation exchangers with carboxylate anions). Here typically the target protein binds to the resin in a buffer solution of low salt concentration at a pH lower than the pI of the target protein (i.e. the charge of the protein is positive). Target protein elution is performed either with an increasing salt gradient, by step elution with a pre-defined pH and salt concentration or by increasing elution buffer pH.

Protein molecules vary considerably in their charge properties and exhibit different degrees of interaction with charged chromatography media according to differences in their overall charge, charge density and surface charge distribution. For example, monoclonal antibodies comprise ionizable groups such as carboxyl groups and amino groups. The charge of these groups will depend on the pH. Therefore, depending on the pI of an antibody the charge of a protein molecule can be manipulated by exposing the bulk product to different pH conditions. Both, AEX and CEX, have been demonstrated to be effective in removing not only aggregates but also other impurities.

Fractionation Types

Typically, the separation of dimer and other aggregate species from the target product is challenging because of the similar chemical constitution of these entities. Therefore, the control of the purification process and in particular the selection of the fractionation type are other important aspects besides the choice of the resin (e.g. AEX, CEX, HIC etc.) and the conditions to be applied (e.g. protein load, bind-elute mode or flow-through mode). During 'fixed volume fractionation', the fraction collector continuously collects the eluate and switches tubes according to a defined set volume throughout the entire elution step. This type of fractionation is also known as straight fractionation (FIG. 1A). On the other hand, 'peak fractionation' can be used to increase the purity of the collected protein peaks and minimize the number of tubes used (FIG. 1B). Combination of 'fixed volume' and 'peak' fractionation can also be applied and allows fractions collected by 'fixed volume fractionation' and fractions collected by 'peak fractionation' to be directed to different collection tubes. During 'peak fractionation' separation of aggregates and/or impurities from the target protein is indirectly controlled using specific peak start and stop collection criteria. Several parameters are available as peak cut criteria for starting and terminating peak collection during elution. In industrial scale manufacturing, typical peak cut parameters are a specific A280 absorbance signal (measured at UV 280 nm), conductivity or pH and are pre-defined as threshold criteria for starting and stopping collecting the eluate. The challenge on the one hand is the determination of optimal cut points (threshold criteria) for the start and the end of product eluate collection, such that product recovery is maximal and aggregate and/or impurity concentrations are not present or very low and within the specification. Furthermore, the determination of these points is hampered due to the potential variance of elution peak shapes of the sample to be purified under different elution conditions.

Figure 2:
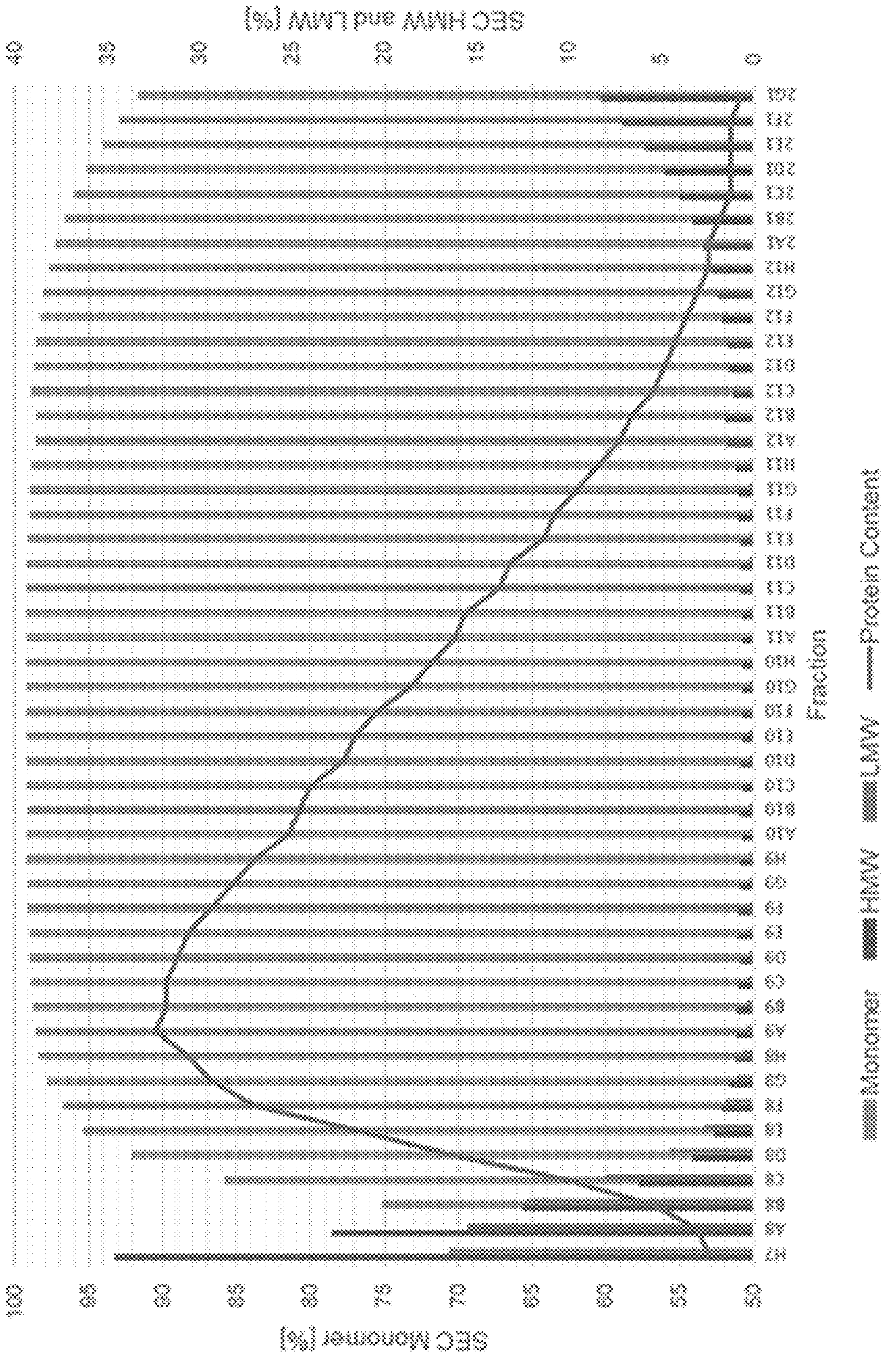
FIG. 2. Representative chromatogram of an elution run during CEX polishing. Antibody monomer content (left Y-Axis) and HMW and LMW aggregates/impurities (right Y-Axis) of eluate fractions (X-Axis) are shown. Aggregates/impurities accumulate at the beginning of the elution peak (Fractions H7, A8, B8, C8, D8, E8, F8, G8).

Peak cut criteria can easily be set only if aggregates/impurities to be removed from a target protein are well baseline separated from the target protein, e.g. by a wash step, so that the target protein 'elutes' distinguishable from the aggregates/impurities as a separate peak. In these cases, the signal for eluate collection is usually set at a low absorbance value, often based on a percentage of the maximum height that the elution peak achieves, in the ascending part of the elution peak. However, for samples where no clean separation between the target protein and aggregates/impurities exists with an accumulation of aggregates/impurities at the front of a peak (e.g. a linear gradient without clear separation of peaks) (FIG. 2), the determination of an optimal start for collection is difficult. In particular, charged variants and aggregated forms of proteins still pose a significant challenge for purification processes. In addition, process parameters (e.g. pH of the elution buffer, amount of protein loaded onto the column), typically vary within a certain range and may directly affect the shape (i.e. width and height) of the peak. Choosing a peak start criterion (e.g. absorbance) too low leads to an ineffective removal of impurities for higher and/or narrower peaks, whereas choosing a peak start criterion too high, leads to reduced yields for lower and/or broader peaks. If the defined A280 signal is not to be reached at all, consequently, no sample will be collected and the whole target protein is lost. Therefore, the determination of a universally valid start point for eluate collection, which can be used efficaciously over a range of conditions resulting in eluates of equal or similar quality, is a difficult and challenging task. The solution to this problem is reflected in the claims explained herein and illustrated in the Examples and Figures.

Embodiments

The present disclosure is directed to an improved method for eluting antibodies from a chromatography resin during purification. In particular, the disclosure relates to a method for the determination of an absorbance signal A0, which is used as reference signal to obtain the starting signal for collecting the eluate at a predetermined interval D0 after the absorbance signal A0 is reached, comprising the steps of a) receiving elution peak chromatograms of at least two different elution runs ($ER_1, \ldots, ER_N$) with the protein sample to be purified, wherein the different elution runs vary in pH, load density or salt conditions, and
b) specifying an absorbance value A0 in the elution peaks, wherein A0 is in the range of 10-50% of the absorbance signal at peak maximum of each elution peak, and the same between each elution peak of ER1, . . . , $ER_N$.

In another embodiment, the disclosure relates to a method for determining an absorbance signal A0, which is to be used as reference for an improved starting point for collection of eluate fractions in chromatography of an antibody sample, comprising the following steps:

a) determining elution peak chromatograms of at least two different elution runs ($ER_1, \ldots, ER_N$) with the antibody sample, wherein the different elution runs vary in pH, load density or salt conditions,
b) specifying an absorbance signal ($A_1, \ldots, A_N$) in each of said different elution run chromatograms, wherein
   i) the numerical difference of the absorbance signal ($A_1, \ldots, A_N$) to the absorbance signal at peak maximum of the respective elution peak ($A_{MAX}1, \ldots A_{MAX}N$) is not more than 300 mAU, and wherein
   ii) the corresponding eluate fraction collected at this absorbance signal ($A_1, \ldots, A_N$) is characterized by an aggregate/impurity content below 10%.
c) normalizing the elution peak chromatograms according the flow volumes of said absorbance signals specified in step b),
d) overlaying the normalized elution peak chromatograms, and
e) determining an absorbance signal A0, wherein A0 is in the ascending part of the elution peaks and is the same at the corresponding column volume between the normalized elution peaks.

In other embodiments the difference of the absorbance signal to the absorbance signal at peak maximum $A_{MAX}$ of the respective elution peak in step b) is not more than 150 mAU, not more than 200 mAU, not more than 250 mAU, not more than 300 mAU, not more than 400 mAU, not more than 500 mAU, not more than 600 mAU, not more than 700 mAU.

In other embodiments the distance of $A_1, \ldots, A_N$ to the absorbance signal $A_{MAX}$ at height maximum of the corresponding elution peak is in the range of 0 to 150 mAU, 0 to 200 mAU, 0 to 250 mAU, 0 to 300 mAU, 0 to 400 mAU, 0 to 500 mAU, 0 to 600 mAU, 0 to 700 mAU measured at 280 nm.

In other embodiments, the corresponding eluate fraction of the absorbance signal ($A_1, \ldots, A_N$) in step b) is characterized by an aggregate/impurity content below 9%, below 8%, below 7%, below 6%, below 5%, below 4%, below 3%, below 2%, or below 1%. In a preferred embodiment, the aggregate/impurity content relates to HMW and LMW species.

In another embodiment, a method is provided for eluting an antibody from a chromatography resin by setting an optimal start point for eluate collection with efficient separation of the target antibody from aggregates and/or impurities, such as higher molecular weight multimer species (dimers, oligomers, aggregates), lower molecular species (clips, etc.) and other contaminants.

The present disclosure is also directed to a method for the purification of an antibody from a chromatography resin, comprising the following steps: a) loading the resin with a sample comprising an antibody and aggregates/impurities, b) optionally, washing the resin with a wash buffer, c) applying an elution buffer, and d) collecting the antibody eluate, wherein the collection of the eluate is started at least 0.1 CV flow volumes after the flow volume C0 of a predetermined absorbance value A0 at an absorbance signal AX. In further embodiments, the collection of the eluate is started at least 0.2 CV, at least 0.3 CV, at least 0.4 CV, at least 0.5 CV, at least 0.6 CV, at least 0.7 CV, at least 0.8 CV, at least 0.9 CV, at least 1.0 CV, at least 1.1 CV, at least 1.2, at least 1.3 CV, at least 1.4 CV, at least 1.5, at least 1.6, at least 1.7 CV, at least 1.8 CV, at least 1.9 CV, at least 2.0 CV at least 2.1 CV, at least 2.2 CV, at least 2.3 CV at least 2.4 CV, at least 2.5 CV, at least 2.6 CV, at least 2.7 CV, at least 2.8 CV, at least 2.9 CV, at least 3.0 CV after the flow volume C0 of A0 at an absorbance signal AX.

In other embodiments the flow volume interval D0 at which collecting the antibody eluate is started is 0.1 CV, is 0.2 CV, is 0.3 CV, is 0.4 CV, is 0.5 CV, is 0.6 CV, is 0.7 CV, is 0.8 CV, is 0.9 CV, is 1.0 CV, is 1.1 CV, is 1.2 CV, is 1.2 CV, is 1.4 CV, is 1.5 CV, is 1.6 CV, is 1.7 CV, is 1.8 CV, is 1.9 CV, is 2.0 CV, is 2.1 CV, is 2.2 CV, is 2.3 CV, is 2.4 CV, is 2.5 CV, is 2.6 CV, is 2.7 CV, is 2.8 CV, is 2.9 CV, is 3.0 CV after the flow volume C0 of A0 at an absorbance signal AX.

In a further embodiment, the present disclosure provides a method for eluting an antibody from a chromatography resin, wherein the method comprises one or more ion exchange chromatography steps, characterized in that the start of peak fractionation (i.e. collection of the eluate) is 0.1-1.8 CV flow volumes after the flow volume C0 of A0 at an absorbance signal AX.

In a particular embodiment, the present disclosure provides a method for eluting an antibody, wherein the method comprises one or more cation exchange chromatography steps, characterized in that the start of peak fractionation (i.e. collection of the eluate) is 0.1-1.8 CV flow volumes after the flow volume C0 of A0 at an absorbance signal AX.

In all embodiments described herein, the absorbance signal AX might be varying between individual elution peaks of the different elution runs $ER_1, \ldots, ER_N$.

Also disclosed is a method for antibody elution during chromatography wherein the eluate is collected with a delay of at least 0.1 to 3.0 CV flow volume, preferably 0.4 to 1.2 CV after a predetermined flow volume of an absorbance signal A0, wherein said absorbance signal A0 is the absorbance at the first intersection point of the at least two chromatographic elution peaks obtained by at least two different elution runs with different pH or load density conditions in overlaid and normalized chromatograms. Preferably, normalization is according to flow volume.

In another embodiment said elution runs are at different pH and load density conditions.

In one embodiment, the present disclosure provides a method for eluting an antibody, wherein the method comprises a mixed mode chromatography step following affinity chromatography. This mixed mode step can feature either cation or anion exchange or a combination of both. This step can be based on a single type of ion exchanger mixed mode procedure or can include multiple ion exchanger mixed mode steps such as a cation exchange mixed mode step followed by an anion exchange mixed mode step or vice versa. In one embodiment, the ion exchange mixed mode step is a one-step procedure.

In a particular embodiment, the ion exchange mixed mode step involves a two-step ion exchange mixed mode process. A suitable cation exchange column is a column whose stationary phase comprises anionic groups. An example of such a column is a Capto MMC™, Capto MMC™ ImpRes (GE Healthcare), Nuvia™ cPrime™ (Biorad).

In another embodiment, a suitable anion exchange column is a column whose stationary phase comprises cationic groups. An example of such a column is a Capto Adhere™, and Capto Adhere™ ImpRes (GE Healthcare).

In one embodiment, the affinity chromatography step comprises subjecting the primary recovery sample to a column comprising a suitable affinity chromatographic support. Examples of such chromatographic supports include, but are not limited to Protein A, Protein G, Protein L, affinity supports comprising the antigen against which the antibody of interest was raised, and affinity supports comprising other Fc binding molecules. In particular, Protein A is useful for affinity purification of IgG antibodies. In certain aspects, Protein A is selected from ProSep® Ultra Plus Protein A, MabSelect SuRe™ Protein A, and Amsphere Protein A™ resins. In one aspect, a Protein A column is equilibrated with a suitable buffer prior to sample loading. An example of a suitable buffer is PBS, pH 7.0-7.3. Following this equilibration, the sample is loaded onto the column. Following the loading of the column, the column is washed one or multiple times using, e.g., the equilibrating buffer. Other washes employing different buffers can be used before eluting the column. The Protein A column can then be eluted using an appropriate elution buffer. An example of a suitable elution buffer comprises Na-Acetate buffer, pH around 3.6.

In one embodiment, the affinity chromatography eluate is prepared for multimodal CEX by adjusting the pH and ionic strength of the sample buffer. For example, the affinity eluate can be adjusted to a pH of about 4.5 to about 7.0 with a load density of about 10 to about 200 g/L. Preferably, the pH is from 4.95 to 5.65 and load density from 20 to 40 g/L. Prior to loading the affinity eluate sample onto the multimodal CEX column, the column can be equilibrated using a suitable buffer. An example of a suitable buffer is 20 mM Na-Acetate, 20 mM MES, pH 5.5. Following equilibration, the column is loaded with the affinity eluate. Following loading, the column is washed one or multiple times with a suitable buffer. An example of a suitable buffer is the equilibration buffer itself. In another embodiment, the affinity eluate is prepared for a mixed mode chromatography step under similar conditions.

One embodiment of the present invention is directed toward a method of purifying an antibody from a sample such that the resulting antibody eluate is substantially free of process- and product-related impurities including host cell proteins, DNA, leached Protein A, aggregates, HMW species, LMW species and fragments.

In one embodiment, the present disclosure provides a method for purification of a cell culture derived antibody or antibody fragment from a crude mixture (that may include HCPs, aggregates and other impurities in addition to the target antibody) and wherein the method comprises an affinity chromatography step and one or more IEX chromatography steps, characterized in that the chromatographic peak cut criteria for starting eluate collection comprise i) a first flow volume time-point C0 at which a first pre-determined A280 signal A0, as reference is reached and ii) a second column volume time-point CX, at which a second A280 signal (AX) is reached, at which target protein eluate collection is started. The difference between CX and C0 corresponds to a predetermined flow volume interval D0.

In one embodiment, the flow volume difference between CX and C0 is in the range from 0.1 to 2.5 CV flow volume. In other embodiments, the difference between CX and C0 is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 CV flow volume.

In one aspect, a pH gradient is used for elution during cation exchange chromatography for the characterization of the antibody. In one embodiment, the pH gradient ranges from 4.9 to 7.0.

In another aspect, a linear salt gradient is used for elution. In one embodiment, the salt gradient ranges from 100 to 500 mM.

In one embodiment of the present disclosure, the antibody to be purified is a human, humanized or chimeric antibody.

In certain embodiments of the present invention, the antibody to be purified is an IgA1, IgA2, IgD, IgE, IgG1, IgG2, IgG3, IgG4, or IgM isotype antibody and variants thereof.

In preferred embodiments, the antibody to be purified is an IgG1 antibody.

In one embodiment, the present disclosure refers to a method for the purification of an antibody or antibody fragment specific for IL-17C. In another embodiment, the present disclosure refers to a method for the purification of an antibody or antibody fragment specific for IL-17C wherein said antibody or antibody fragment comprises:

a HCDR1 region comprising the amino acid sequence of SEQ ID No.: 1, a HCDR2 region comprising the amino acid sequence of SEQ ID No.: 2, a HCDR3 region comprising the amino acid sequence of SEQ ID No.: 3, a LCDR1 region comprising the amino acid sequence of SEQ ID No.: 4, a LCDR2 region comprising the amino acid sequence of SEQ ID No.: 5 and a LCDR3 region comprising the amino acid sequence of SEQ ID No.: 6.

In another embodiment the present disclosure refers to a method for the purification of an antibody or antibody fragment specific for IL-17C wherein said antibody or antibody fragment comprises the HCDR1 region of SEQ ID No.: 1, the HCDR2 region of SEQ ID No.: 2, the HCDR3 region of SEQ ID No.: 3, the LCDR1 region of SEQ ID No.: 4, the LCDR2 region of SEQ ID No.: 5 and the LCDR3 region of SEQ ID No.: 6.

In one embodiment, the present disclosure refers to a method for the purification of an antibody comprising a variable heavy chain and a variable light chain comprising a heavy chain and a light chain that have at least 90%, at least 91%, at least 92%, at least 93%, at least 94%, at least 95%, at least 96%, at least 97%, at least 98% or at least 99% sequence identity to the variable heavy chain of SEQ ID No.: 8 and to the variable light chain of SEQ ID No.: 7.

In a further embodiment, the present disclosure refers to a method for the purification of an antibody comprising a heavy chain and a light chain that have at least 90%, at least 91%, at least 92%, at least 93%, at least 94%, at least 95%, at least 96%, at least 97%, at least 98% or at least 99% sequence identity to the heavy chain of SEQ ID No.: 10 and to the light chain of SEQ ID No.: 9.

In one embodiment, the present disclosure refers to a method for the purification of an antibody comprising a variable heavy chain of SEQ ID No.: 8 and a variable light chain of SEQ ID No.: 7.

In a further embodiment, the present disclosure refers to a method for the purification of an antibody comprising a heavy chain of SEQ ID No.: 10 and a light chain of SEQ ID No.: 9.

In another embodiment the present disclosure refers to a method for the purification of an antibody or antibody fragment specific for IL-17C wherein said antibody or antibody fragment comprises a HCDR1 region comprising the amino acid sequence of SEQ ID No.: 1, a HCDR2 region comprising the amino acid sequence of SEQ ID No.: 2, a HCDR3 region comprising the amino acid sequence of SEQ ID No.: 3, a LCDR1 region comprising the amino acid sequence of SEQ ID No.: 4, a LCDR2 region comprising the amino acid sequence of SEQ ID No.: 5 and a LCDR3 region comprising the amino acid sequence of SEQ ID No.: 6 and a variable heavy chain and a variable light chain that have at least 90%, at least 91%, at least 92%, at least 93%, at least 94%, at least 95%, at least 96%, at least 97%, at least 98% or at least 99% sequence identity to the variable heavy chain of SEQ ID No.: 8 and the variable light chain of SEQ ID No.: 7.

In another embodiment the present disclosure refers to a method for the purification of an antibody or antibody fragment specific for IL-17C wherein said antibody or antibody fragment comprises a HCDR1 region comprising the amino acid sequence of SEQ ID No.: 1, a HCDR2 region comprising the amino acid sequence of SEQ ID No.: 2, a HCDR3 region comprising the amino acid sequence of SEQ ID No.: 3, a LCDR1 region comprising the amino acid sequence of SEQ ID No.: 4, a LCDR2 region comprising the amino acid sequence of SEQ ID No.: 5 and a LCDR3 region comprising the amino acid sequence of SEQ ID No.: 6 and a heavy chain and a light chain that have at least 90%, at least 91%, at least 92%, at least 93%, at least 94%, at least 95%, at least 96%, at least 97%, at least 98% or at least 99% sequence identity to the heavy chain of SEQ ID No.: 10 and the light chain of SEQ ID No.: 9.

In another embodiment the present disclosure refers to a method for the purification of an antibody or antibody fragment specific for IL-17C wherein said antibody or antibody fragment comprises the HCDR1 region of SEQ ID No.: 1, the HCDR2 region of SEQ ID No.: 2, the HCDR3 region of SEQ ID No.: 3, the LCDR1 region of SEQ ID No.: 4, the LCDR2 region of SEQ ID No.: 5 and the LCDR3 region of SEQ ID No.: 6 and a variable heavy chain and a variable light chain that have at least 90%, at least 91%, at least 92%, at least 93%, at least 94%, at least 95%, at least 96%, at least 97%, at least 98% or at least 99% sequence identity to the variable heavy chain of SEQ ID No.: 8 and the variable light chain of SEQ ID No.: 7.

In another embodiment the present disclosure refers to a method for the purification of an antibody or antibody fragment specific for IL-17C wherein said antibody or antibody fragment comprises the HCDR1 region of SEQ ID No.: 1, the HCDR2 region of SEQ ID No.: 2, the HCDR3 region of SEQ ID No.: 3, the LCDR1 region of SEQ ID No.: 4, the LCDR2 region of SEQ ID No.: 5 and the LCDR3 region of SEQ ID No.: 6 and a heavy chain and a light chain that have at least 90%, at least 91%, at least 92%, at least 93%, at least 94%, at least 95%, at least 96%, at least 97%, at least 98% or at least 99% sequence identity to the heavy chain of SEQ ID No.: 10 and the light chain of SEQ ID No.: 9.

Antibody preparations to which the invention can be applied can include unpurified or partially purified antibodies from natural, synthetic, or recombinant sources. The mixture may be cell culture material, for example, solubilized cells and cell culture supernatant. In certain embodiments, it is a clarified cell culture harvest. In other embodiments the antibody preparation is a Protein A chromatography eluate. In yet another embodiment the mixture is an eluate obtained by an AIEX chromatography step. The methods of the invention can be used as a polishing step to purify an antibody from any mixture containing the antibody.

Further, the present disclosure is directed toward pharmaceutical compositions comprising one or more antibodies purified by the method described herein.

The purity of the antibodies of interest in the resultant sample product can be analyzed using methods well known to those skilled in the art, e.g., size-exclusion chromatography, Poros™ A HPLC Assay, HCP ELISA, Protein A ELISA, and western blot analysis.

In a preferred embodiment, the method provided herein results in a purified antibody having a SEC monomer content of more than or equal to 95.0%, 95.5%, 96.0%, 96.5%, 97.0%, 97.5%, 98.0%, 98.5%, 99.0%, 99.1%, 99.2%, 99.3%, 99.4%, 99.5%, 99.6%, 99.7%, 99.8%, or more than or equal to 99.9%. In another embodiment, the purified protein has a SEC monomer content of 100%.

In another embodiment, the method provided herein results in a purified antibody with a yield of more than or equal to 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or more than or equal to 99%.

In a preferred embodiment, the disclosure relates to a method for the purification of an antibody by chromatography, comprising the following steps:

a) loading a sample comprising an antibody onto a chromatography resin,
b) optionally, washing the resin,
c) applying an elution buffer to the chromatography resin, and
d) starting collection of the eluate, wherein the collection of the eluate is started at a predetermined interval (D0) after the absorbance signal of the eluate has reached a predetermined value (A0).

In another embodiment, the predetermined value (A0) is in the range of 10-50% of the absorbance signal at peak maximum of elution peaks obtained by different elution runs with the antibody sample to be purified. Said different elution runs vary in pH, load density or salt conditions. Preferably, the varying conditions are within a range of pH 5 to pH 7 and within a range of 5 to 50 g/L resin load.

In a preferred embodiment, the predetermined absorbance value (A0) is in the range of 0 to 1500 mAU measured at 280 nm. In another embodiment the predetermined absorbance value (A0) is about 700 mAU measured at 280 nm. In yet another embodiment A0 is in the ascending part of the elution peak.

In another embodiment, the disclosure relates to a method according to any of the preceding, wherein the predetermined interval (D0) is a flow volume interval that is determined by the following steps:

a) receiving the elution peak chromatograms of at least two different elution runs ($ER_1, \ldots, ER_N$) with the antibody sample to be purified, wherein the different elution runs vary in pH, load density or salt conditions,
b) specifying an absorbance signal $A_1, \ldots, A_N$ for each of the elution peaks received in step a), wherein each of the corresponding eluate fractions of $A_1, \ldots, A_N$ has an aggregate/impurity content below 5%,
c) determining the flow volumes $C_1, \ldots C_N$ of the absorbance signals $A_1, \ldots, A_N$ for each of the elution runs in the chromatograms,
d) calculating the difference for each of said flow volumes $C_1, \ldots, C_N$, to the flow volume C0 of A0, and
e) averaging said differences (i.e. obtaining the mean value), thereby obtaining the predetermined flow volume interval (D).

In a preferred embodiment, the distance of $A_1, \ldots, A_N$ to the individual absorbance signals $A_{MAX}$ at height maximum of the corresponding elution peaks is in the range of 0 to 100 mAU measured at 280 nm.

In another embodiment, the predetermined interval value (D0) is between 0.4 to 1.2 CV flow volumes or the predetermined interval value (D0) is 0.6 CV flow volumes.

In a preferred embodiment, the chromatography is ion exchange (IEX) chromatography. Preferably, the chromatography is cation exchange (CEX) chromatography. Most preferably, the chromatography is multimodal CEX.

In a preferred embodiment, the present disclosure refers to a method for the purification of an antibody by multimodal cation exchange (CEX) chromatography, comprising the following steps:

a) loading a sample comprising said antibody onto a multimodal CEX chromatography resin,
b) optionally, washing the resin,
c) applying an elution buffer to the multimodal CEX chromatography resin, and
d) starting collection of the eluate, wherein the collection of the eluate is started at a predetermined interval (D0) of 0.6 CV flow volumes after the absorbance signal of the eluate has reached a predetermined value (A0) of 700 mAU measured at 280 nm and wherein said antibody comprises a heavy chain of SEQ ID NO: 10 and a light chain of SEQ ID NO: 9.

In another embodiment the present disclosure refers to a method for the purification of an antibody specific for IL-17C by multimodal cation exchange (CEX) chromatography, comprising the following steps:

a) loading a sample comprising said antibody onto a multimodal CEX chromatography resin,
b) optionally, washing the resin,
c) applying an elution buffer to the multimodal CEX chromatography resin, and
d) starting collection of the eluate, wherein the collection of the eluate is started at a predetermined interval (D0) of 0.6 CV flow volumes after the absorbance signal of the eluate has reached a predetermined value (A0) of 700 mAU measured at 280 nm and wherein said antibody comprises a HCDR1 region comprising the amino acid sequence of SEQ ID No.: 1, a HCDR2 region comprising the amino acid sequence of SEQ ID No.: 2, a HCDR3 region comprising the amino acid sequence of SEQ ID No.: 3, a LCDR1 region comprising the amino acid sequence of SEQ ID No.: 4, a LCDR2 region comprising the amino acid sequence of SEQ ID No.: 5 and a LCDR3 region comprising the amino acid sequence of SEQ ID No.: 6 and a variable heavy chain and a variable light chain that have at least 90%, at least 91%, at least 92%, at least 93%, at least 94%, at least 95%, at least 96%, at least 97%, at least 98% or at least 99% sequence identity to the variable heavy chain of SEQ ID No.: 8 and the variable light chain of SEQ ID No.: 7.

In another embodiment, the present disclosure refers to a method for the purification of an antibody specific for IL-17C by multimodal cation exchange (CEX) chromatography, comprising the following steps:

a) loading a sample comprising said antibody onto a multimodal CEX chromatography resin,
b) optionally, washing the resin,
c) applying an elution buffer to the multimodal CEX chromatography resin, and
d) starting collection of the eluate, wherein the collection of the eluate is started at a predetermined interval (D0) of 0.6 CV flow volumes after the absorbance signal of the eluate has reached a predetermined value (A0) of 700 mAU measured at 280 nm and wherein said antibody comprises a HCDR1 region comprising the amino acid sequence of SEQ ID No.: 1, a HCDR2 region comprising the amino acid sequence of SEQ ID No.: 2, a HCDR3 region comprising the amino acid sequence of SEQ ID No.: 3, a LCDR1 region comprising the amino acid sequence of SEQ ID No.: 4, a LCDR2 region comprising the amino acid sequence of SEQ ID No.: 5 and a LCDR3 region comprising the amino acid sequence of SEQ ID No.: 6 and a heavy chain and a light chain that have at least 90%, at least 91%, at least 92%, at least 93%, at least 94%, at least 95%, at least 96%, at least 97%, at least 98% or at least 99% sequence identity to the heavy chain of SEQ ID No.: 10 and the light chain of SEQ ID No.: 9.

Definitions

The term "protein" as used herein refers a sequential chain of amino acids linked together via peptide bonds. The term is used to refer to an amino acid chain of any length, and can refer to a minimal chain comprising two amino acids linked together via a peptide bond. As used herein, a "peptide," a "peptide fragment," a polypeptide"," an "amino acid chain," an "amino acid sequence," or any other term used to refer to a chain or chains of two or more amino acids, are generically included in the definition of a "protein". The term further includes proteins, which have undergone post-translational modifications, for example, glycosylation, acetylation, phosphorylation, or amidation. Any protein that is expressible in a host cell can be expressed and purified in accordance with the present invention. For example, the present disclosure can be employed to purify an enzyme, receptor, antibody, antibody fragment, hormone, regulatory factor, cytokine antigen, binding agent, fusion protein, alternative scaffold protein and the like.

A "buffer" is a solution that resists changes in pH by the action of its acid-base conjugate components. Various buffers, which can be employed depending, for example, on the desired pH of the buffer are described in Buffers. A Guide for the Preparation and Use of Buffers in Biological Systems, Gueffroy, D., ed. Calbiochem Corporation (1975). Non-limiting examples of buffers that will control the pH in this range include MES, MOPS, MOPSO, Tris, HEPES, phosphate, acetate, citrate, succinate, and ammonium buffers, as well as combinations of these.

The term "elution buffer" refers to the buffer, which is typically used to remove (elute) the polypeptide (analyte) from the purification device (e.g. a chromatographic resin) to which it was applied earlier. Typically, the elution buffer is selected so that separation of the polypeptide of interest from unwanted aggregates/impurities can be accomplished. Often, the concentration of a particular ingredient, such as a particular salt (e.g. NaCl) in the elution buffer is varied during the elution procedure (gradient). The gradient may be continuous (linear) or stepwise (interrupted by hold periods).

The term "linear salt gradient" refers to varying salt concentration (ionic strength) with time during the gradient buffer used during elution. Typically, samples are loaded in a low salt environment to promote interaction with the stationary phase. Commonly used salts are sodium and potassium chloride and acetate. An adequate salt concentration is required to disrupt the stationary phase/analyte interaction in order to elute the analyte. Typical elution concentrations are in the range 100-500 mM.

The term "isoelectric point (pI)" is the pH at which a particular molecule or surface carries no net electrical charge. The pI of a polypeptide is dependent on the amino acids that make up the polypeptide. At a pH below its pI, the polypeptide carries a net positive charge. At a pH above its pI, the polypeptide carries a net negative charge. A polypeptide can therefore be separated based on its ionization status at a given pH. The actual pI of a polypeptide can be affected by factors such as post-translational modification and can be determined by experimental methods such as isoelectric focusing.

The term "chromatography" refers to any current or future chromatography-based process of purifying one or more target molecules from a sample, e.g. by the removal of aggregates and/or impurities and/or other non-target molecules. During chromatography a solute of interest, for example a polypeptide, in a mixture is separated from other solutes in the mixture as a result of differences in rates at which the individual solutes of the mixture migrate through a stationary medium under the influence of a moving phase, or in bind and elute processes. Examples of chromatography include, but are not limited to: affinity chromatography, immobilized metal ion affinity chromatography, flow-through chromatography, ion exchange chromatography, size-exclusion chromatography, reversed-phase chromatography, simulated moving-bed chromatography, hydrophobic interaction chromatography, gel filtration, chromato-focusing.

The term "mixed mode chromatography" or "multimodal chromatography" refers to a purification process using mixed mode adsorbents, which provide multiple modes of interaction, such as hydrophobic, cation exchange, and hydrogen bonding interaction between the polypeptide of interest and the adsorbent ligands. Commercially available mixed mode chromatography resins include Capto™ MMC, Capto™ MMC ImpRes, Capto Blue, Blue Sepharose™ 6 Fast Flow, Capto™ Adhere, and Capto™ Adhere ImpRes from GE Healthcare Life Sciences or Eshmuno® HCX from EMD Millipore, or Nuvia™ cPrime from Bio-Rad.

The terms "cation exchange resin" or "cation exchange adsorbent" refer to a solid phase which is negatively charged, and which thus has free cations for exchange with cations in an aqueous solution passed over or through the solid phase. A negatively charged ligand attached to the solid phase to form the cation exchange resin may be, e.g. a carboxylate or sulfonate. Commercially available cation exchange resins include carboxy-methyl-cellulose, sulphopropyl (SP) immobilized on agarose (e.g. SP Sepharose™ XL, SP-Sepharose™ Fast Flow, SP Sepharose™ High Performance, CM Sepharose™ Fast Flow, CM Sepharose™ High Performance, Capto™ S, and Capto™ SP ImpRes from GE Healthcare Life Sciences, or Fractogel® EMD SE HiCap, Fractogel® EMD SO3", Fractogel® EMD COO", Eshmuno™ S, and Eshmuno™ CPX from EMD Millipore, or UNOsphere™ S and Nuvia™ S from Bio-Rad).

The terms "anion exchange resin" or "anion exchange adsorbent" are used herein to refer to a solid phase, which is positively charged, e.g. having one or more positively charged ligands, such as quaternary amino groups, attached thereto. Commercially available anion exchange resins include DEAE Sepharose™ Fast Flow, Q Sepharose™ Fast Flow, 0 Sepharose™ High Performance, Q Sepharose™ XL, Capto™ DEAE, Capto™ Q, and Capto™ Q ImpRes from GE Healthcare Life Sciences, or Fractogel® EMD TMAE HiCap, Fractogel® EMD DEAE, and Eshmuno Q from EMD Millipore, or U Osphere™ Q and Nuvia™ 0 from Bio-Rad.

The term "chromatogram" refers to a graphical representation of one or more output parameters as registered during at least a part of the chromatography purification process. The chromatogram may present the output parameter as a function of time, accumulated column volume or any other parameter relevant for the chromatography purification. In the present method, each purification is registered as a chromatogram by monitoring an output parameter during the purification. The term "output parameter" refers to a registerable parameter that is indicative of the result of a chromatography purification. Examples of output parameters include but are not limited to: UV absorbance at one or more wavelengths, conductivity, light scattering detection, fluorescence emission, mass-spectroscopy, registered flow, registered pH, registered pressure. The output parameter is suitably measured in line in the flow path downstream of the chromatography purification. A0, $A_1, \ldots, A_N$, AX, and $A_{MAX}$ as used herein correspond to absorbance signals. C0, $C_1, \ldots, C_N$, CX and $C_{MAX}$ are the corresponding flow volumes (column volumes) of A0, $A_1, \ldots, A_N$, AX and $A_{MAX}$, respectively.

The term "ascending part of an elution peak" refers to signals above baseline before the maximum peak height is reached. Correspondingly, the descending part of an elution peak refers to signals after the peak maximum above baseline.

The term "antibody" refers to glycosylated and non-glycosylated immunoglobulins of any of the five major classes (isotypes) of immunoglobulins: IgA, IgD, IgE, IgG, and IgM, or subclasses thereof (e.g., IgG1, IgG2, IgG3, IgG4, IgA1 and IgA2) and combinations and variants thereof. As used herein, the term encompasses antibodies from any species (e.g. human, murine, canine, feline, equine, bovine, galline, etc.) and combinations or variants thereof (e.g. humanized, chimeric antibodies). The term refers to monoclonal and polyclonal antibodies as well as to monospecific and multi-specific antibodies (such as bispecific antibodies). As used herein, the term also encompasses fusion proteins comprising an antigen determination portion, and any other modified immunoglobulin molecule comprising an antigen recognition site. As used herein, the term "antibody" includes intact immunoglobulins as well as antibody fragments, that refer to one or more portions of an antibody that retain the ability to specifically interact with (e.g., by binding, steric hindrance, stabilizing spatial distribution) an antigen. Examples of binding fragments include, but are not limited to Fab, Fab', F(ab')2, Fd, Fv and dAb fragments (Ward et al., (1989) Nature 341:544-546), single chain Fv (scFv) (e.g., Bird et al., (1988) Science 242:423-426; and Huston et al., (1988) Proc. Natl. Acad. Sci. 85:5879-5883). Any naturally occurring, enzymatically obtainable, synthetic, alternative scaffold, or genetically engineered polypeptide that specifically binds an antigen to form a complex are also intended to be encompassed within the term "antibody" as used herein.

The terms "contaminant" and "impurity" are used interchangeably herein and refer to any objectionable molecule, including a biological macromolecule such as DNA, RNA, one or more host cell proteins, endotoxins, lipids and one or more additives which may be present in a sample containing the target protein that is being separated from one or more of the foreign or objectionable molecules using a process of the present invention. Additionally, such a contaminant may include any reagent, which is used in a step that may occur prior to the purification process.

"High molecular weight (HMW) species" include species having a higher molecular weight than the target protein mass, such as multimers. Multimers include everything other than the monomer of the target protein. For instance, a monomer of an IgG antibody encompasses the traditional tetrameric antibody composition comprising two heavy and light chains. Multimers include species having a higher molecular mass than the target protein mass, such as dimers (two identical proteins associated covalently or non-covalently) and aggregates (covalent or non-covalently associated complete and/or partial proteins).

"Low molecular weight (LMW) species" include species having a lower molecular weight than the target protein mass, such as clips, and degraded product.

As used herein, the term "polishing" refers to a downstream processing step after the initial (affinity) capture step, which is intended to remove residual amounts of aggregates and/or impurities. The aggregates/impurities removed during polishing typically have more similarity to the product than the impurities removed during the capture step.

Methods for the determination of yield and purity of a polypeptide are known to those of skill in the art. Yield and purity of a polypeptide may be determined by any suitable method of analysis (e.g., band intensity on a silver stained gel, polyacrylamide gel electrophoresis, ELISA, HPLC and the like). An exemplary method is size-exclusion chromatography (SEC) high-performance liquid chromatography (HPLC). Purity may be determined e.g. using relative "area under the curve" (AUC) values, which can typically be obtained for peaks in a chromatogram, such as an HPLC chromatogram. Optionally, purities are determined by chromatographic or other means using a standard curve generated using a reference material of known purity. Purity may also be determined on a weight-by-weight basis.

The term "bind and elute mode" refers to a product separation technique in which at least one product contained in a sample (e.g., an Fc region containing protein, an antibody) binds to a chromatographic resin or media and is subsequently eluted.

The term "absorption" refers to the physical process of absorbing light, while "absorbance" is the mathematical measure of the quantity of light absorbed by a sample per sample length at a given wavelength λ. It is also known as optical density (OD) or extinction. Many substances absorb ultraviolet (UV) or visible (VIS) light due to their chemical composition. The UV range covers 190-380 nm and the VIS range 380-770 nm. In proteins, for example, the peptide bond absorbs light at 215 nm and the aromatic group on certain amino acids absorbs at 280 nm. The absorption of light by substances has been used for detecting the presence of, and measuring the concentration of such substances. Typical units of absorbance are called "absorbance units", "AU" and are dimensionless. Absorbance is calculated based on either the amount of light reflected or scattered by a sample or by the amount transmitted through a sample. If all light passes through a sample, none was absorbed, so the absorbance would be zero and the transmission would be 100%. On the other hand, if no light passes through a sample, the absorbance is infinite and the percent transmission is zero. The Beer-Lambert law, $A=\varepsilon \times b \times c$, is used to calculate absorbance at a given wavelength, where A is absorbance (dimensionless, $A=\log_{10} P0/P$), P0 is intensity of the incident light, P is intensity of the transmitted light, e is the molar absorptivity or molar attenuation coefficient (M-1 cm-1), b is the path length of the sample (e.g. length of a cuvette (cm)), c is the molar concentration of a solute in solution (mol/L). Absorbance units as used herein are determined at a wavelength of UV 280 nm and at a path length of 0.2 cm.

The term "predetermined absorbance value A0" relates to a pre-set, pre-decided fixed absorbance signal in the elution peak, which is equal between the different elution runs $ER_1, \ldots, ER_N$ of a defined antibody sample.

C0 is the corresponding flow volume of absorbance value A0 for each individual elution peak of the elution runs ($ER_1, \ldots, ER_N$) (measurement unit is 'column volume', CV) in each chromatogram (C0 might be different between different elution runs $ER_1, \ldots, ER_N$).

$A_1, \ldots, A_N$ are absorbance values determined for each of the elution peaks of the elution runs $ER_1, \ldots, ER_N$ with a corresponding eluate fraction showing either no aggregates/impurities or showing an aggregate/impurity content below 10% or showing an aggregate/impurity content within the specification.

AX is the absorbance value at which eluate collection is effectively started (AX might be different between different elution runs $ER_1, \ldots, ER_N$). Preferably, AX has a greater value than A0 (AX>A0).

CX is the flow volume at which eluate collection is effectively started (CX might be different between different elution runs). CX is reached at the predetermined flow volume interval D0 after C0 and can be calculated by the formula CX=C0+D0.

The term "predetermined interval (D0)" refers to a predetermined flow volume interval. Preferably, D0 is calculated by averaging (i.e. obtaining the mean value) the differences of the flow volumes $C_1, \ldots, C_N$ to the flow volume of A0 (which is C0). $C_1, \ldots, C_N$ are the flow volumes of the absorbance signals $A_1, \ldots, A_N$ in the elution peak chromatograms of the at least two different elution runs ($ER_1, \ldots, ER_N$) with the protein sample to be purified, wherein the different elution runs vary in pH, load density or salt conditions, wherein each of the corresponding eluate fractions of $A_1, \ldots, A_N$ has an aggregate/impurity content below 10%, below 7.5%, below 5%, below 4.5%, below 4%, below 3.5%, below 3%. Alternatively, the median might be used to describe the middle of the set of differences (e.g. if that set has an outlier). D0 can also be defined as a pre-decided interval without any calculation.

The amino acid and encoding nucleic acid sequences in Table 1 are an example of an IL-17C antibody, as well as portions thereof.

TABLE 1

Exemplary IL-17C antibody sequences

| Antibody | | SEQ ID No.: | [aa]/[DNA] |
|---|---|---|---|
| MAB#1 | HCDR1 | SEQ ID No.: 1 | DYAMH |
| | HCDR2 | SEQ ID No.: 2 | YIGGVGEGTQYAESVKG |
| | HCDR3 | SEQ ID No.: 3 | GFAIRYYGFDY |
| | LCDR1 | SEQ ID No.: 4 | SGDKLGDKYAY |
| | LCDR2 | SEQ ID No.: 5 | QDSKRPS |
| | LCDR3 | SEQ ID No.: 6 | QVFTFPLVTT |
| | VL | SEQ ID No.: 7 | SYELTQPPSVSVSPGQTASITCSGDKLGDKYAYWYQ QKPGQSPVLVIYQDSKRPSGIPERFSGSNSGNTATL TISGTQAEDEADYYCQVFTFPLVTTVFGGGTKLTVLG Q |
| | VH | SEQ ID No.: 8 | EVQLLESGGGLVQPGGSLRLSCAASGFTVSDYAMH WVRQAPGKGLEWVSYIGGVGEGTQYAESVKGRFTI SRDNSKNTLYLQMNSLRAEDTAVYYCARGFAIRYYG FDYWGQGTLVTVSS |
| | Light chain | SEQ ID No.: 9 | SYELTQPPSVSVSPGQTASITCSGDKLGDKYAYWYQ QKPGQSPVLVIYQDSKRPSGIPERFSGSNSGNTATL TISGTQAEDEADYYCQVFTFPLVTTVFGGGTKLTVLG QPKAAPSVTLFPPSSEELQANKATLVCLISDFYPGAV TVAWKADSSPVKAGVETTTPSKQSNNKYAASSYLSL TPEQWKSHRSYSCQVTHEGSTVEKTVAPTECS |
| | Heavy chain (IgG1) | SEQ ID No.: 10 | EVQLLESGGGLVQPGGSLRLSCAASGFTVSDYAMH WVRQAPGKGLEWVSYIGGVGEGTQYAESVKGRFTI SRDNSKNTLYLQMNSLRAEDTAVYYCARGFAIRYYG FDYWGQGTLVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KRVEPKSCDKTHTCPPCPAPELLGGPSVFLFPPKPK DTLMISRTPEVTCVVVDVSHEDPEVKFNWYVDGVEV HNAKTKPREEQYNSTYRVVSVLTVLHQDWLNGKEY KCKVSNKALPAPIEKTISKAKGQPREPQVYTLPPSRE EMTKNQVSLTCLVKGFYPSDIAVEWESNGQPENNY KTTPPVLDSDGSFFLYSKLTVDKSRWQQGNVFSCSV MHEALHNHYTQKSLSLSPGK |
| | VL | SEQ ID No.: 11 | TCCTACGAGCTGACCCAGCCCCCCTCCGTGTCCG TGTCTCCTGGCCAGACCGCCTCCATCACCTGTTCC |

TABLE 1-continued

Exemplary IL-17C antibody sequences

| Antibody | SEQ ID No.: | [aa]/[DNA] |
|---|---|---|
| | | GGCGACAAGCTGGGCGATAAGTACGCCTACTGGT<br>ATCAGCAGAAGCCCGGCCAGTCCCCCGTGCTGGT<br>CATCTACCAGGACTCCAAGCGGCCCTCCGGCATC<br>CCTGAGCGGTTCTCCGGCTCCAACTCCGGCAACA<br>CCGCCACCCTGACCATCTCCGGCACCCAGGCCGA<br>GGACGAGGCCGACTACTACTGCCAGGTGTTCACC<br>TTCCCCCTGGTCACCACCGTGTTCGGCGGAGGCA<br>CCAAGCTGACCGTGCTGGGCCAG |
| VH | SEQ ID No.: 12 | GAGGTGCAGCTGCTGGAATCCGGCGGAGGACTG<br>GTGCAGCCTGGCGGCTCCCTGAGACTGTCTTGCG<br>CCGCCTCCGGCTTCACCGTGTCCGACTACGCTAT<br>GCACTGGGTCCGACAGGCCCCTGGCAAGGGCCT<br>GGAATGGGTGTCCTATATCGGCGGCGTGGGCGAG<br>GGCACCCAGTACGCTGAGTCTGTGAAGGGCCGGT<br>TCACCATCTCCCGGGACAACTCCAAGAACACCCT<br>GTACCTGCAGATGAACTCCCTGCGGGCCGAGGAC<br>ACCGCCGTGTACTACTGTGCCAGAGGCTTCGCCA<br>TCCGGTACTACGGCTTCGACTACTGGGGCCAGGG<br>CACCCTGGTCACCGTGTCTAGC |
| Light chain | SEQ ID No.: 13 | TCCTACGAGCTGACCCAGCCCCCCTCCGTGTCCG<br>TGTCTCCTGGCCAGACCGCCTCCATCACCTGTTCC<br>GGCGACAAGCTGGGCGATAAGTACGCCTACTGGT<br>ATCAGCAGAAGCCCGGCCAGTCCCCCGTGCTGGT<br>CATCTACCAGGACTCCAAGCGGCCCTCCGGCATC<br>CCTGAGCGGTTCTCCGGCTCCAACTCCGGCAACA<br>CCGCCACCCTGACCATCTCCGGCACCCAGGCCGA<br>GGACGAGGCCGACTACTACTGCCAGGTGTTCACC<br>TTCCCCCTGGTCACCACCGTGTTCGGCGGAGGCA<br>CCAAGCTGACCGTGCTGGGCCAGCCTAAGGCCGC<br>TCCCTCCGTGACCCTGTTCCCCCCATCCTCCGAG<br>GAACTGCAGGCCAACAAGGCCACCCTGGTCTGCC<br>TGATCTCCGACTTCTACCCTGGCGCCGTGACCGT<br>GGCCTGGAAGGCCGACAGCTCTCCTGTGAAGGCC<br>GGCGTGGAAACCACCACCCCCTCCAAGCAGTCCA<br>ACAACAAATACGCCGCCTCCTCCTACCTGTCCCTG<br>ACCCCCGAGCAGTGGAAGTCCCACCGGTCCTACA<br>GCTGCCAGGTCACACACGAGGGCTCCACCGTGGA<br>AAAGACCGTGGCCCCTACCGAGTGCTCC |
| Heavy chain (IgG1) | SEQ ID No.: 14 | GAGGTGCAGCTGCTGGAATCCGGCGGAGGACTGGTGC<br>AGCCTGGCGGCTCCCTGAGACTGTCTTGCGCCGCCTC<br>CGGCTTCACCGTGTCCGACTACGCTATGCACTGGGTCC<br>GACAGGCCCCTGGCAAGGGCCTGGAATGGGTGTCCTA<br>TATCGGCGGCGTGGGCGAGGGCACCCAGTACGCTGAG<br>TCTGTGAAGGGCCGGTTCACCATCTCCCGGGACAACTC<br>CAAGAACACCCTGTACCTGCAGATGAACTCCCTGCGGG<br>CCGAGGACACCGCCGTGTACTACTGTGCCAGAGGCTT<br>CGCCATCCGGTACTACGGCTTCGACTACTGGGGCCAG<br>GGCACCCTGGTCACCGTGTCTAGCGCCTCCACCAAGG<br>GCCCCTCCGTGTTCCCTCTGGCCCCCTCCAGCAAGTCC<br>ACCTCTGGCGGCACCGCTGCCCTGGGCTGCCTGGTCA<br>AGGACTACTTCCCCGAGCCCGTGACCGTGTCCTGGAAC<br>TCTGGCGCCCTGACCTCCGGCGTGCACACCTTCCCTG<br>CCGTGCTGCAGTCCTCCGGCCTGTACTCCCTGTCCTCC<br>GTCGTGACCGTGCCCTCCAGCTCTCTGGGCACCCAGA<br>CCTACATCTGCAACGTGAACCACAAGCCCTCCAACACC<br>AAGGTGGACAAGCGGGTGGAACCCAAGTCCTGCGACA<br>AGACCCACACCTGTCCCCCCTGCCCTGCCCCTGAACTG<br>CTGGGCGGACCTTCCGTGTTCCTGTTCCCCCCAAAGCC<br>CAAGGACACCCTGATGATCTCCCGGACCCCCGAAGTGA<br>CCTGCGTGGTGGTGGACGTGTCCCACGAGGACCCTGA<br>AGTGAAGTTCAATTGGTACGTGGACGGCGTGGAAGTGC<br>ACAACGCCAAGACCAAGCCCAGAGAGGAACAGTACAAC<br>TCCACCTACCGGGTGGTGTCCGTGCTGACCGTGCTGC<br>ACCAGGACTGGCTGAACGGCAAAGAGTACAAGTGCAA<br>GGTGTCCAACAAGGCCCTGCCTGCCCCCATCGAAAAGA<br>CCATCTCCAAGGCCAAGGGCCAGCCCCGCGAGCCCCA<br>GGTGTACACACTGCCCCCTAGCCGGGAAGAGATGACC<br>AAGAACCAGGTGTCCCTGACCTGTCTGGTCAAGGGCTT<br>CTACCCCTCCGACATTGCCGTGGAATGGGAGTCCAACG<br>GCCAGCCCGAGAACAACTACAAGACCACCCCCCCTGT<br>GCTGGACTCCGACGGCTCATTCTTCCTGTACTCCAAGC<br>TGACCGTGGACAAGTCCCGGTGGCAGCAGGGCAACGT<br>GTTCTCCTGCTCCGTGATGCACGAGGCCCTGCACAACC<br>ACTACACCCAGAAGTCCCTGTCCCTGAGCCCCGGCAAG |

WORKING EXAMPLES

Example 1. Determination of the Interval D0

Figure 3A:
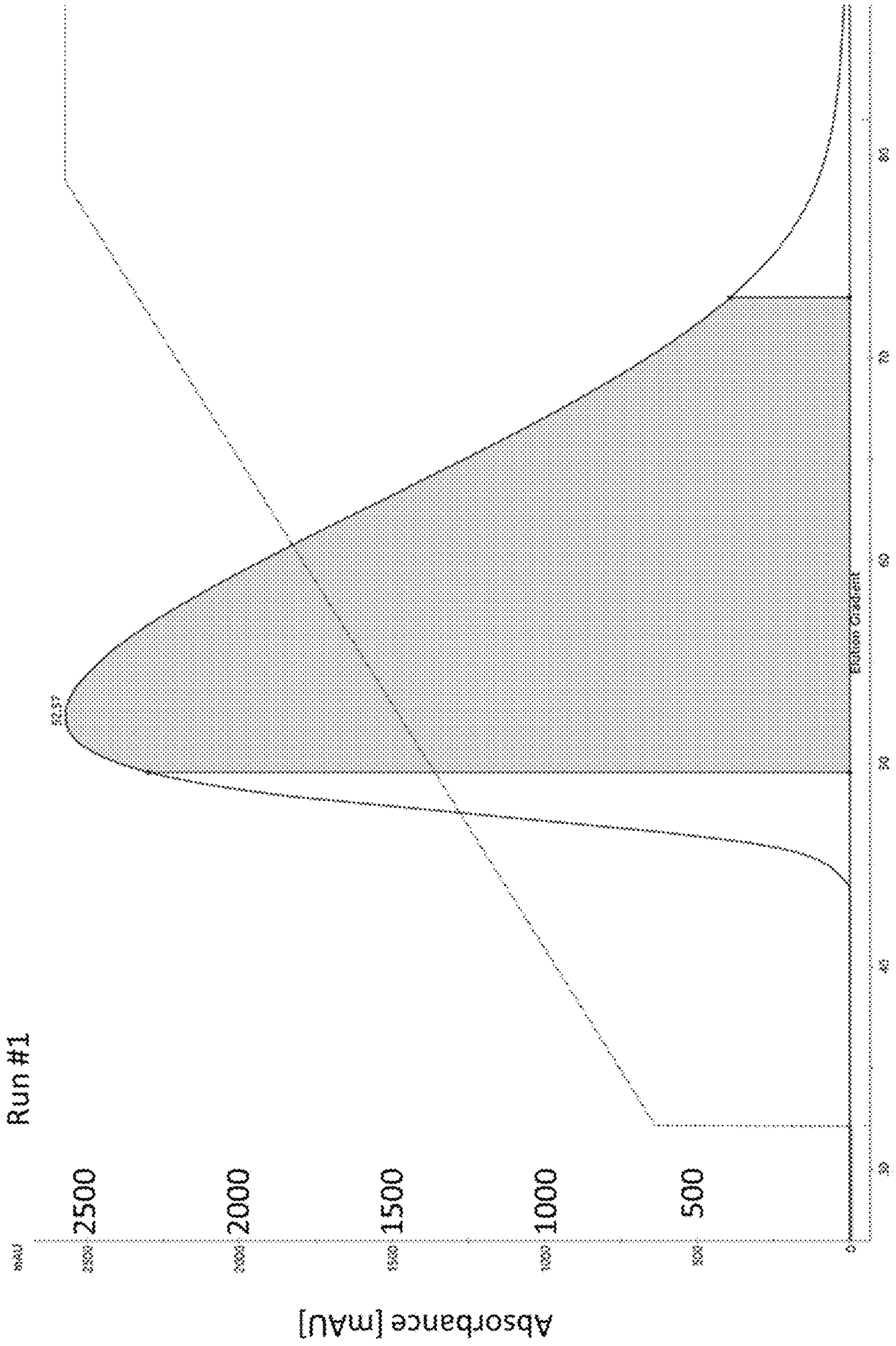
FIGS. 3A-3C. Elution peak chromatograms of three test elution runs ER1, ER2 and ER3, which were used to determine the flow volume interval D0. Shaded segments mark optimal elution pool areas from 2300-400 mAU (for ER1, FIG. 3A), from 1800-400 mAU (for ER2, FIG. 3B) and from 1300-400 mAU (for ER3, FIG. 3C), respectively. Start of eluate collection for each run is at an absorbance signal with a corresponding eluate fraction having aggregates/impurities below 10% (compare FIG. 2).
Figure 3B:
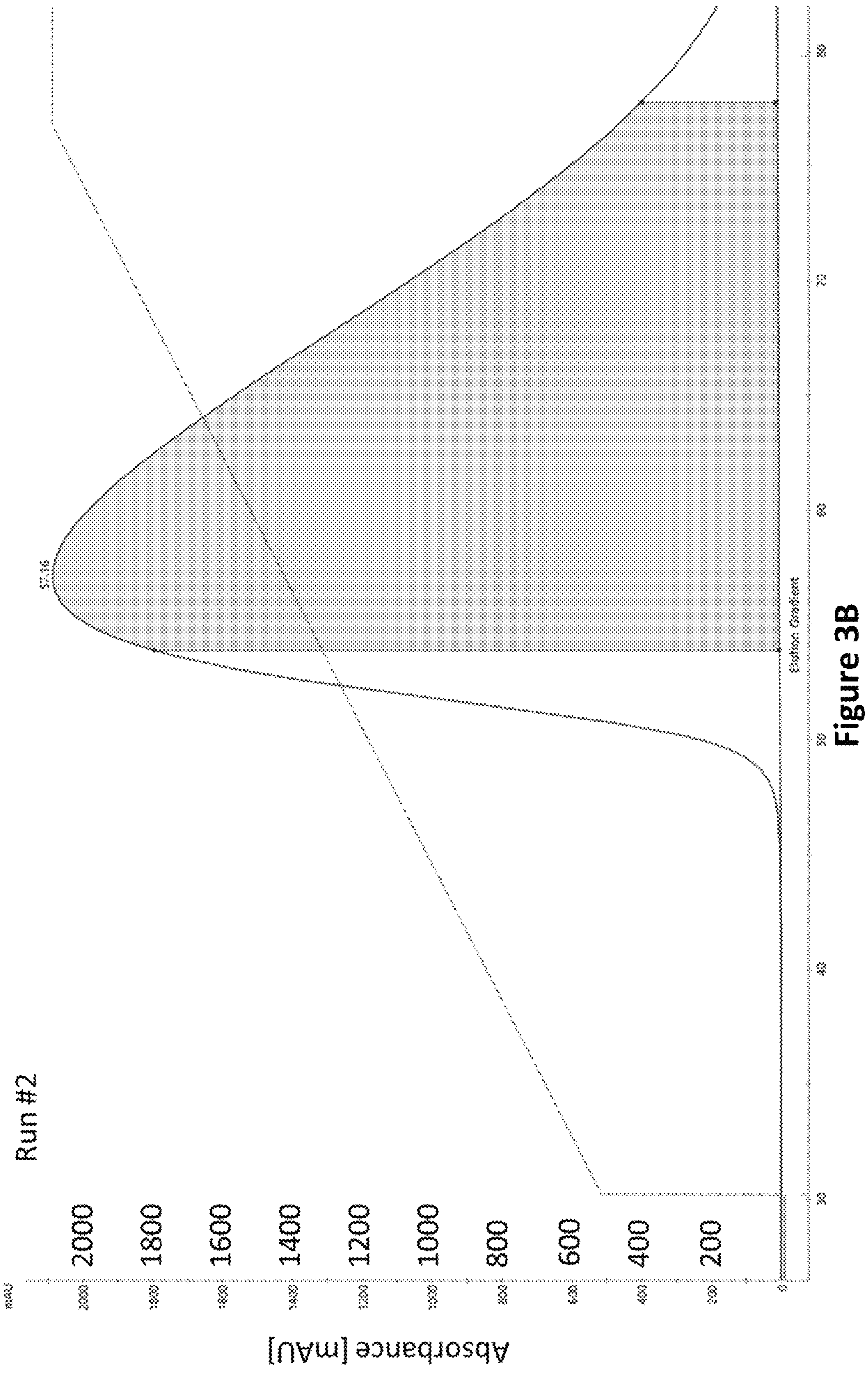
Figure 3C:
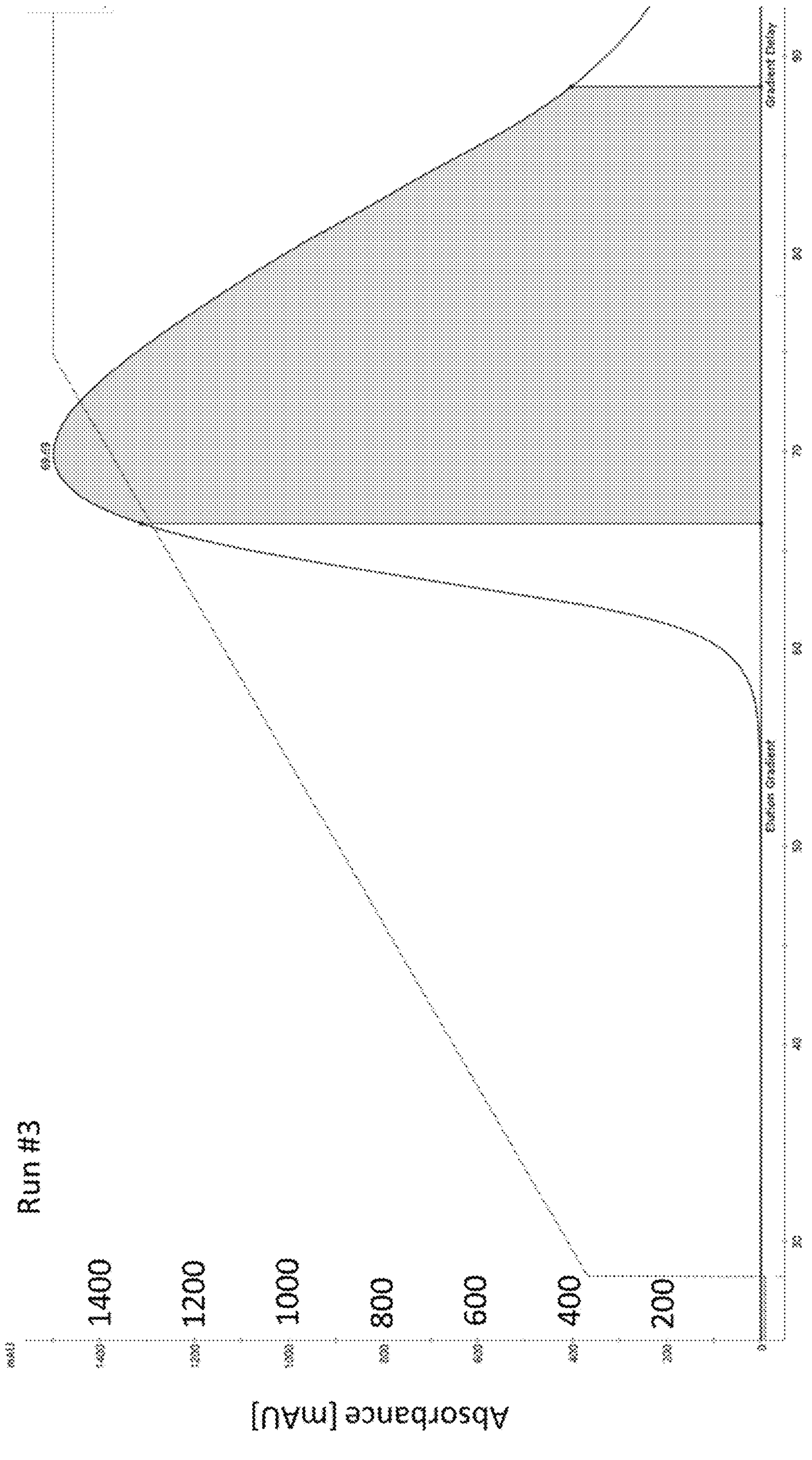

A clarified cell supernatant derived from a mammalian cell culture expressing a recombinant IgG1 in a 3000 L bioreactor was loaded onto a MabSelect SuRe (GE Healthcare) protein A column. The IgG present in the harvest is selectively bound to the protein A. Subsequent to loading, several wash steps are executed. Afterwards, the antibody is eluted from the column in a gradient elution with about 5 column volumes of elution buffer. The elution pool contained the antibody and residual aggregates and impurities of which approximately 2% was dimer, multimer, and aggregate mixture, and about 1% low molecular weight (LMW) contaminants. After a virus inactivation step, a depth filtration step and an AIEX polishing step the IgG sample was loaded on a multimodal CEX column (Capto MMC ImpRes, GE Healthcare) with an ÄKTA avant system in bind-elute mode, followed by a wash step and eluted with a linear salt gradient. Separate test elution runs $ER_1$ to $ER_3$ under different pH and load density conditions were performed as shown in Table 2. 'Peak fractionation' was used to obtain the collected antibody eluate in high purity. To remove residual aggregates/impurities and at the same time maintain a high yield of the target protein, peak collection needs to start at peak maximum or shortly before or after the maximum depending on process conditions and shape of the peak. Absorption signals $A_1$ to $A_3$ for an optimal start of eluate collection of the individual test elution runs and corresponding flow volumes are listed in Table 2. Chromatograms of the elution runs $ER_1$ to $ER_3$ are shown in FIGS. 3A-3C, respectively.

TABLE 2

Gradient buffer pH and sample load amount of three purification test runs $ER_1$ to $ER_3$ of an IgG antibody on Capto MMC ImpRes.

| ER# | Gradient buffer pH | Load amount [g/L resin] | $A_{MAX}$ [mAU] | A0 [mAU] | C0 [CV] | Absorption at eluate collection $A_1, \ldots, A_N$ [mAU] | Flow volume at eluate collection $C_1, \ldots, C_N$ [CV] | Interval $D_1, \ldots, D_N$ = $C_{1,\ldots,N}$ − C0 [CV] |
|---|---|---|---|---|---|---|---|---|
| 1 | 5.65 | 35 | 2570 | 700 | 9.9 | 2300 | 10.6 | 0.7 |
| 2 | 5.50 | 30 | 2087 | 700 | 10.9 | 1800 | 11.5 | 0.6 |
| 3 | 5.35 | 25 | 1498 | 700 | 13.5 | 1300 | 14.1 | 0.6 |

$A_{MAX}$ is the absorbance signal at the maximum height of the elution peak. A0 is the predetermined reference absorbance signal. C0 is the corresponding flow volume of A0. C0 might be different for each individual elution peak as in the present example. Absorption at eluate collection indicates the optimal individual absorbance signals $A_1$, $A_2$, and $A_3$, respectively for starting eluate collection. $C_1$, $C_2$, and $C_3$ are the corresponding flow volumes at eluate collection. $D_1$, $D_2$, and $D_3$ are the individual differences of $C_1$, $C_2$, and $C_3$ and corresponding C0 (Interval). The predetermined interval D0 is obtained by averaging the differences $D_1$, $D_2$, and $D_3$. The mean value here in the present example is (0.7+0.6+0.6)/3=0.63.

Example 2. Use of D0 to Start Eluate Collection

Depending on the pH of the gradient buffer and the protein load per resin volume, the resulting elution peaks differ substantially in width and height and therefore the individual absorption signals for optimal start of eluate collection (Example 1). To apply a consistently robust eluate collection start, an A280 absorbance signal (AX) at a predetermined interval (D0) relative to a reference A280 signal (A0) was used to initiate eluate collection. The pre-determined A280 signal A0 was set to 700 mAU and a 0.6 CV flow volume interval (D0) determined in Example 1 was used to reach an optimal A280 signal (AX) as starting point for eluate collection.

Absorption signals AX, reached after the flow volume interval D0 and at which eluate collection was started are indicated with corresponding flow volumes for each elution run in Table 3.

TABLE 3

Values of CX flow volumes and corresponding absorption signals AX, which are reached after the predetermined flow volume D0, indicated for each Elution run $ER_4$ to $ER_{10}$.

| ER# | Gradient buffer pH | Load amount [g/L resin] | A0 [mAU] | C0 [CV] | Interval D0 [CV] | Flow volume at eluate collection CX [CV] | Absorption at eluate collection AX [mAU] |
|---|---|---|---|---|---|---|---|
| 4 | 5.35 | 20 | 700 | 12.7 | 0.6 | 13.3 | 1523 |
| 5 | 5.35 | 32 | 700 | 12.1 | | 12.7 | 1971 |
| 6 | 5.65 | 20 | 700 | 9.2 | | 9.8 | 2225 |
| 7 | 5.65 | 32 | 700 | 9.2 | | 9.8 | 2887 |
| 8 | 5.50 | 20 | 700 | 10.2 | | 10.8 | 1942 |
| 9 | 5.50 | 32 | 700 | 10.0 | | 10.6 | 2548 |
| 10 | 5.50 | 26 | 700 | 10.0 | | 10.6 | 2344 |

Chromatograms of elution runs $ER_4$ to $ER_{10}$ indicating the peak collection criteria of the invention are shown in FIGS. 4A-4G. The analytical results (yield, HMW, LMW, monomer) are shown in the Figures and as below in Tables 4A-G.

TABLE 4A

Figure 4A:
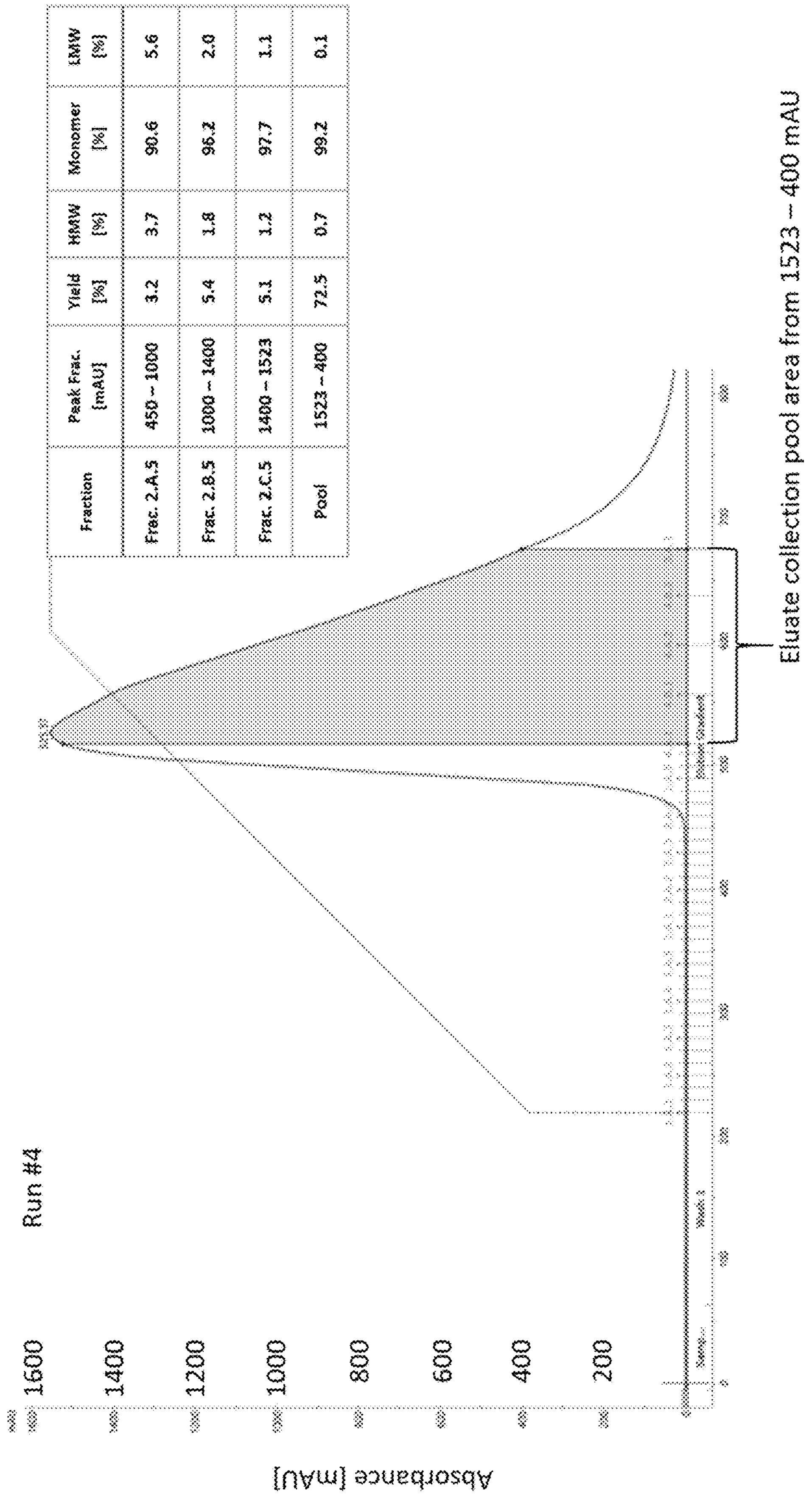
FIGS. 4A-4G. Elution peak chromatograms of different elution runs #4-#10 ($ER_4$ to $ER_{10}$) with varying conditions applying the predetermined flow volume interval D0 for starting collection of the eluate.

Analytical results for Run 4 (109DDA14*1) (FIG. 4A)

| Fraction | Peak Frac. [mAU] | Yield [%] | HMW [%] | Monomer [%] | LMW [%] |
|---|---|---|---|---|---|
| Frac. 2.A.5 | 450-1000 | 3.2 | 3.7 | 90.6 | 5.6 |
| Frac. 2.B.5 | 1000-1400 | 5.4 | 1.8 | 96.2 | 2.0 |
| Frac. 2.C.5 | 1400-1523 | 5.1 | 1.2 | 97.7 | 1.1 |
| Pool | 1523-400 | 72.5 | 0.7 | 99.2 | 0.1 |

TABLE 4B

Figure 4B:
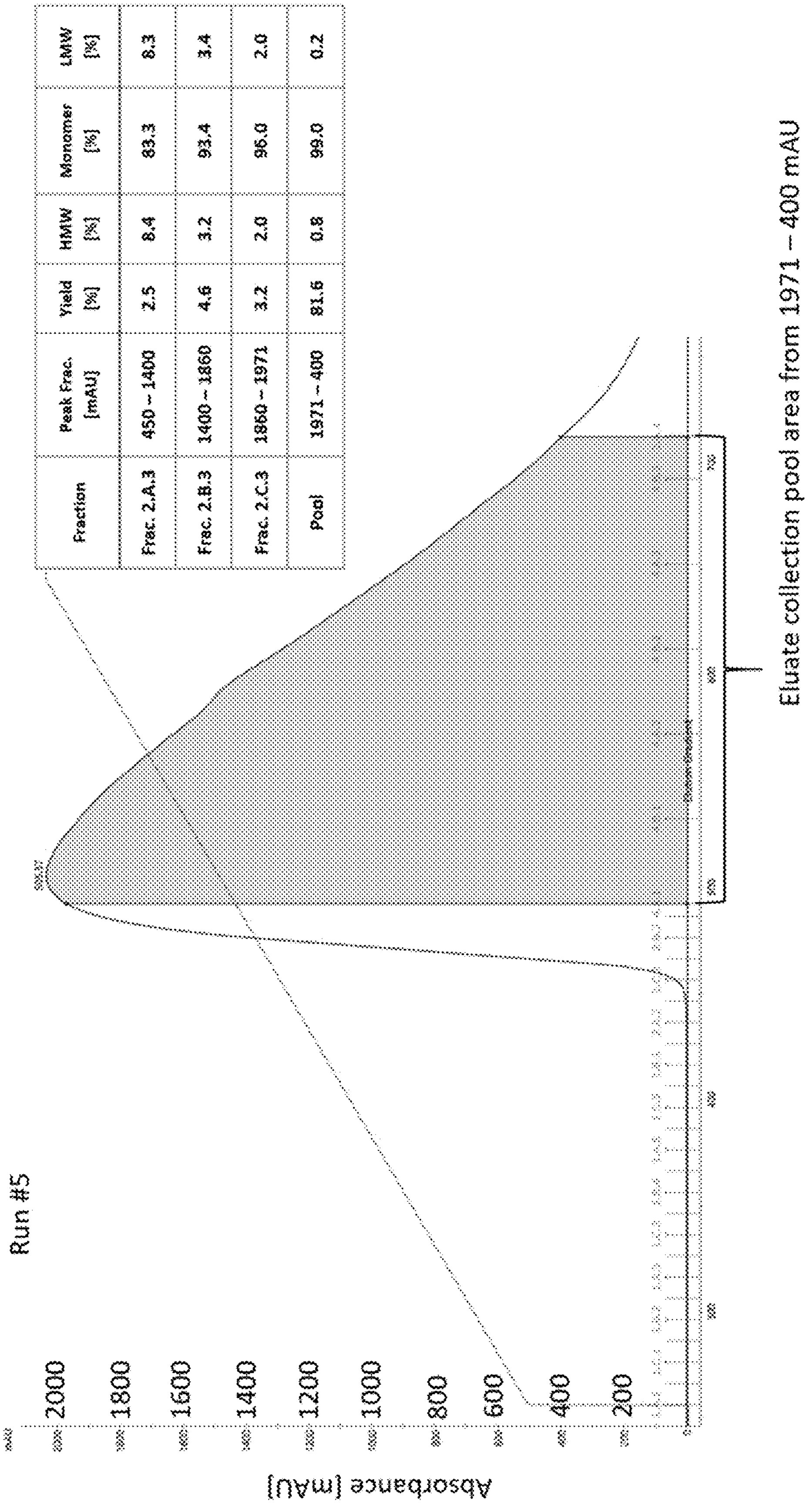

Analytical results for Run 5 (109DDA14*2) (FIG. 4B)

| Fraction | Peak Frac. [mAU] | Yield [%] | HMW [%] | Monomer [%] | LMW [%] |
|---|---|---|---|---|---|
| Frac. 2.A.3 | 450-1400 | 2.5 | 8.4 | 83.3 | 8.3 |
| Frac. 2.B.3 | 1400-1860 | 4.6 | 3.2 | 93.4 | 3.4 |
| Frac. 2.C.3 | 1860-1971 | 3.2 | 2.0 | 96.0 | 2.0 |
| Pool | 1971-400 | 81.6 | 0.8 | 99.0 | 0.2 |

TABLE 4C

Figure 4C:
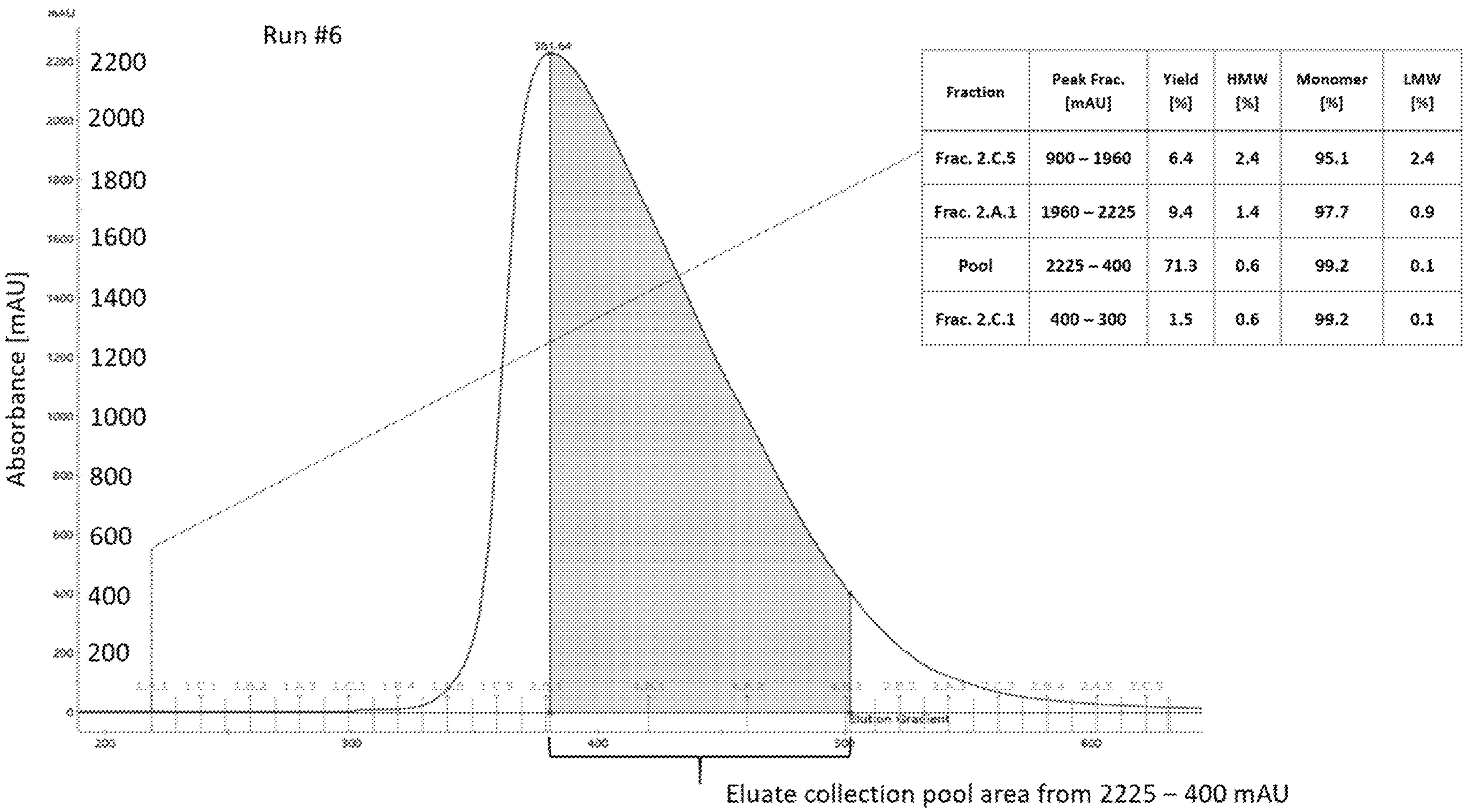

Analytical results for Run 6 (109DDA14*3) (FIG. 4C)

| Fraction | Peak Frac. [mAU] | Yield [%] | HMW [%] | Monomer [%] | LMW [%] |
|---|---|---|---|---|---|
| Frac. 2.C.5 | 900-1960 | 6.4 | 2.4 | 95.1 | 2.4 |
| Frac. 2.A.1 | 1960-2225 | 9.4 | 1.4 | 97.7 | 0.9 |
| Pool | 2225-400 | 71.3 | 0.6 | 99.2 | 0.1 |
| Frac. 2.C.1 | 400-300 | 1.5 | 0.6 | 99.2 | 0.1 |

TABLE 4D

Figure 4D:
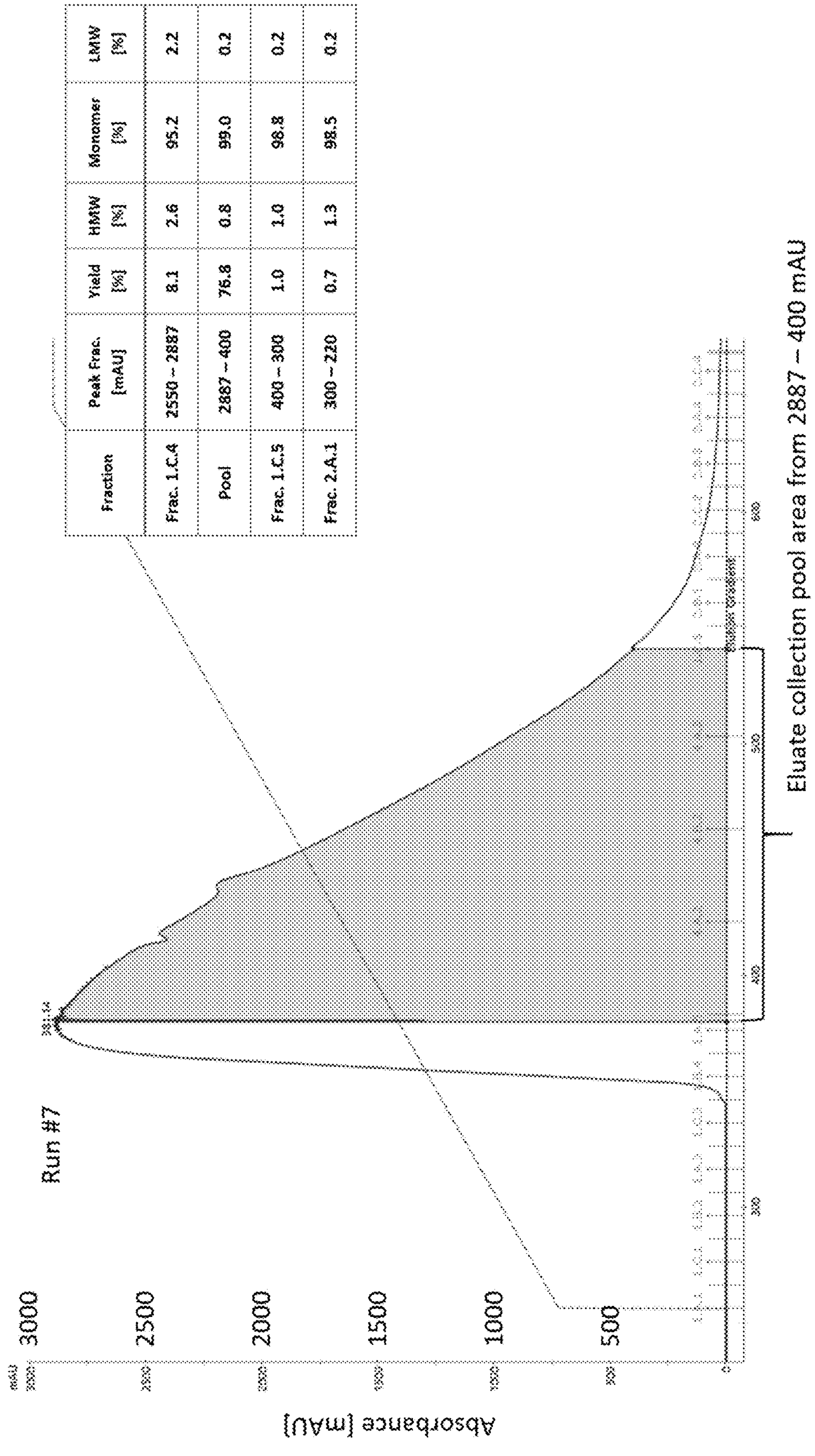
Figure 4E:
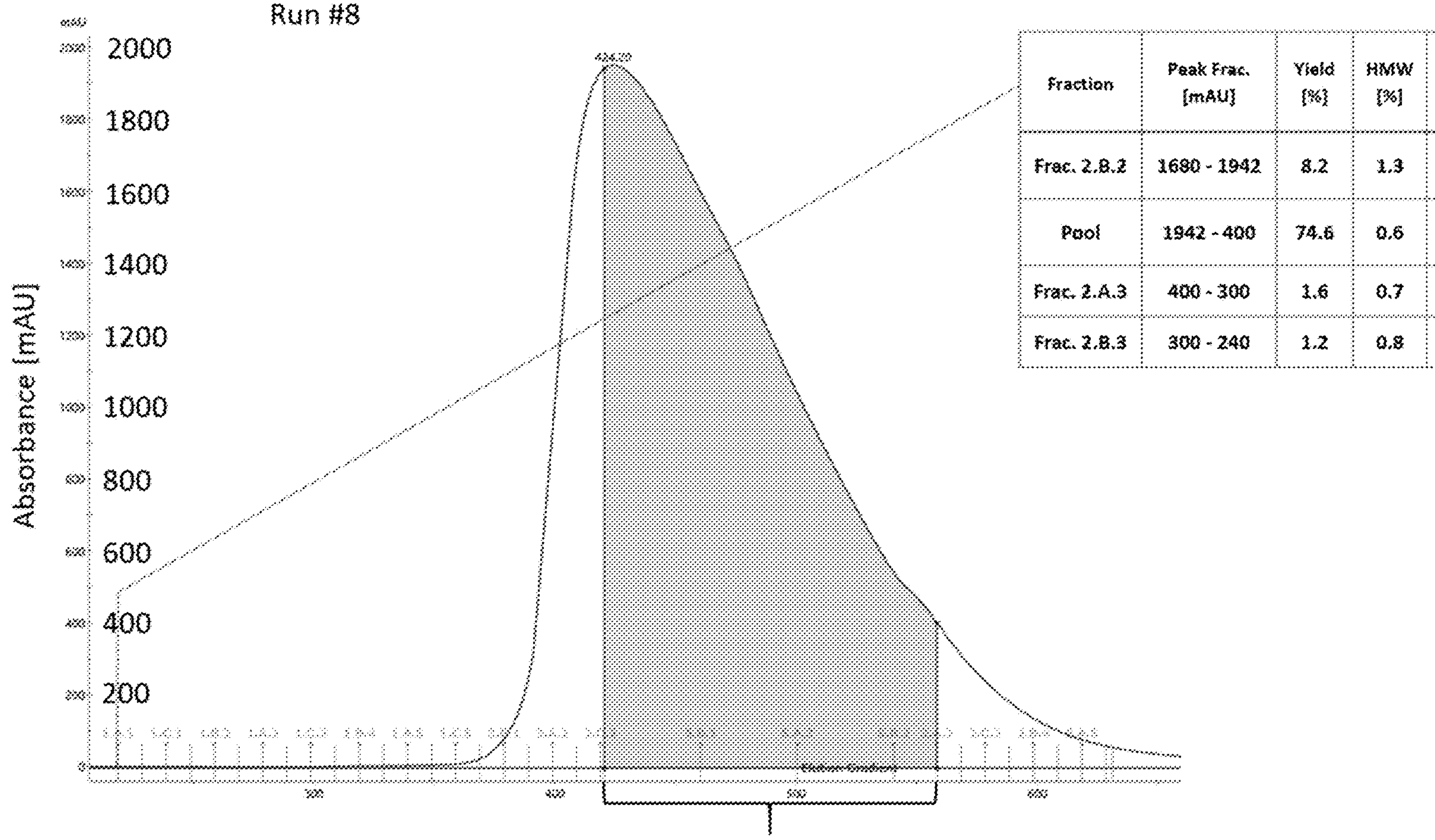
Figure 4F:
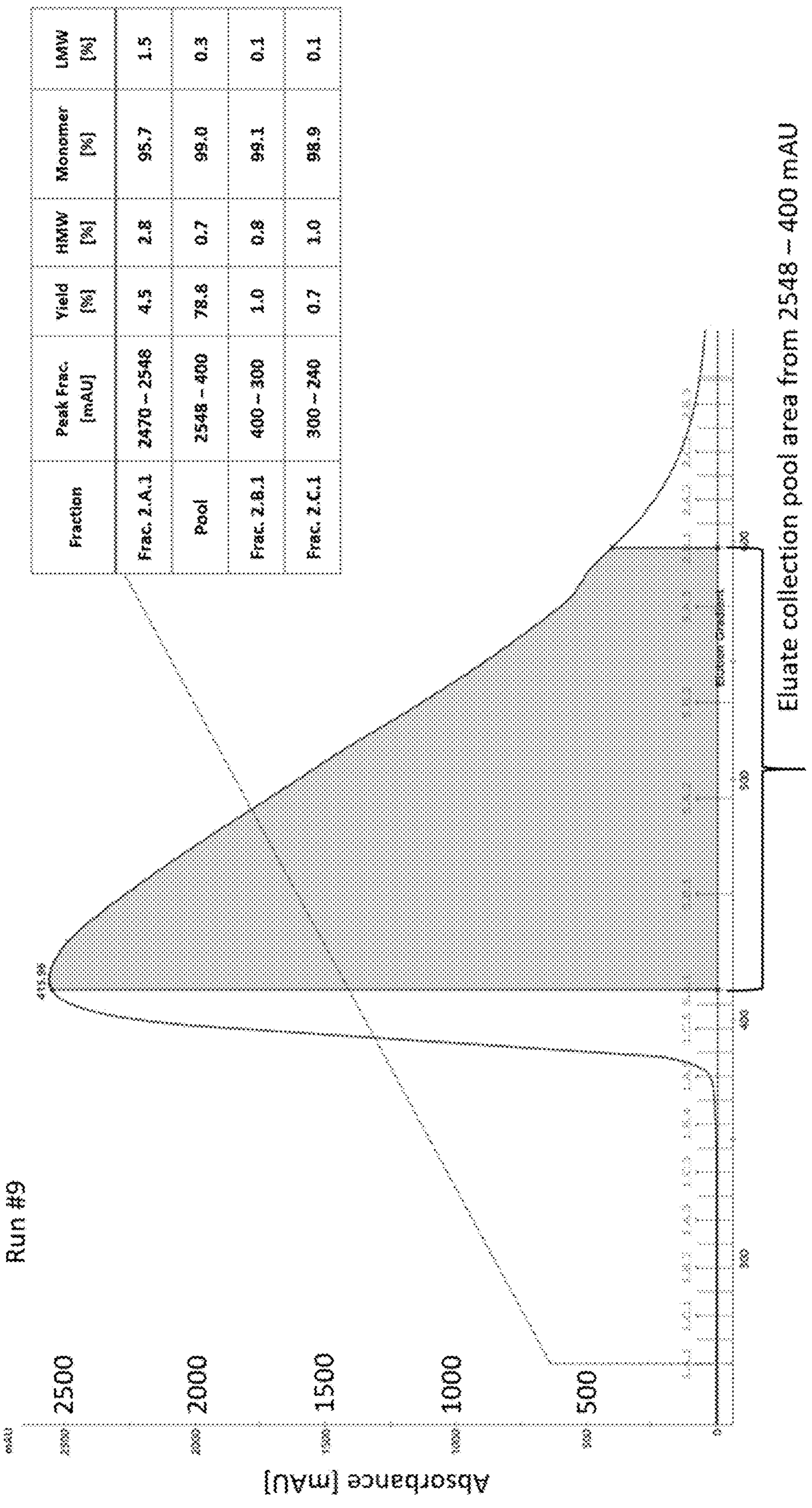
Figure 4G:
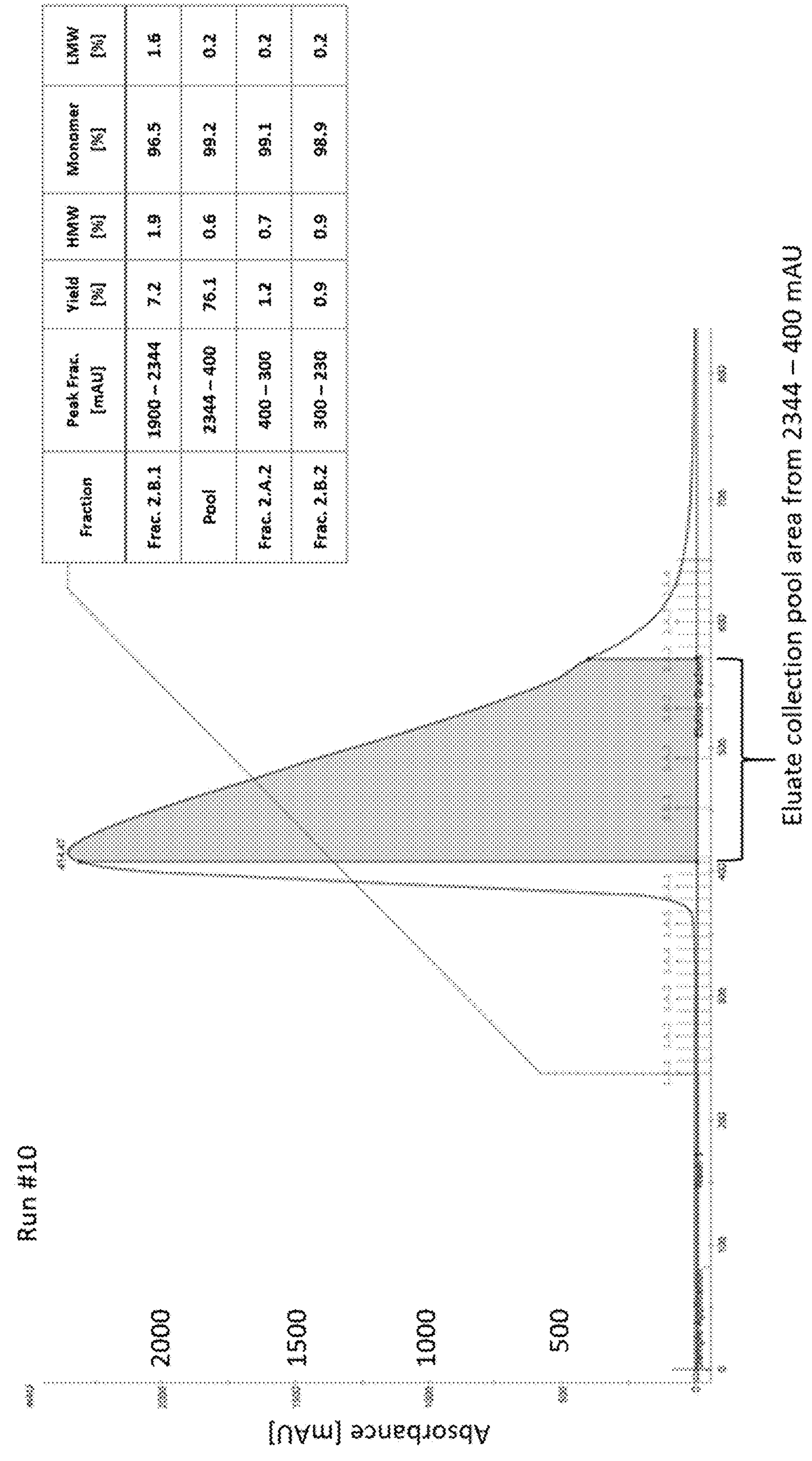

Analytical results for Run 7 (109DDA14*4) (FIG. 4D)

| Fraction | Peak Frac. [mAU] | Yield [%] | HMW [%] | Monomer [%] | LMW [%] |
|---|---|---|---|---|---|
| Frac. 1.C.4 | 2550-2887 | 8.1 | 2.6 | 95.2 | 2.2 |
| Pool | 2887-400 | 76.8 | 0.8 | 99.0 | 0.2 |

TABLE 4D-continued

| Analytical results for Run 7 (109DDA14*4) (FIG. 4D) | | | | | |
|---|---|---|---|---|---|
| Fraction | Peak Frac. [mAU] | Yield [%] | HMW [%] | Monomer [%] | LMW [%] |
| Frac. 1.C.5 | 400-300 | 1.0 | 1.0 | 98.8 | 0.2 |
| Frac. 2.A.1 | 300-220 | 0.7 | 1.3 | 98.5 | 0.2 |

TABLE 4E

| Analytical results for Run 8 (101DGE05*1) (FIG. 4E) | | | | | |
|---|---|---|---|---|---|
| Fraction | Peak Frac. [mAU] | Yield [%] | HMW [%] | Monomer [%] | LMW [%] |
| Frac. 2.B.2 | 1680-1942 | 8.2 | 1.3 | 97.7 | 0.9 |
| Pool | 1942-400 | 74.6 | 0.6 | 99.2 | 0.2 |
| Frac. 2.A.3 | 400-300 | 1.6 | 0.7 | 99.2 | 0.1 |
| Frac. 2.B.3 | 300-240 | 1.2 | 0.8 | 99.1 | 0.1 |

TABLE 4F

| Analytical results for Run 9 (101DGE05*2) (FIG. 4F) | | | | | |
|---|---|---|---|---|---|
| Fraction | Peak Frac. [mAU] | Yield [%] | HMW [%] | Monomer [%] | LMW [%] |
| Frac. 2.A.1 | 2470-2548 | 4.5 | 2.8 | 95.7 | 1.5 |
| Pool | 2548-400 | 78.8 | 0.7 | 99.0 | 0.3 |
| Frac. 2.B.1 | 400-300 | 1.0 | 0.8 | 99.1 | 0.1 |
| Frac. 2.C.1 | 300-240 | 0.7 | 1.0 | 98.9 | 0.1 |

TABLE 4G

| Analytical results for Run 10 (101DGE05*3) (FIG. 4G) | | | | | |
|---|---|---|---|---|---|
| Fraction | Peak Frac. [mAU] | Yield [%] | HMW [%] | Monomer [%] | LMW [%] |
| Frac. 2.B.1 | 1900-2344 | 7.2 | 1.9 | 96.5 | 1.6 |
| Pool | 2344-400 | 76.1 | 0.6 | 99.2 | 0.2 |
| Frac. 2.A.2 | 400-300 | 1.2 | 0.7 | 99.1 | 0.2 |
| Frac. 2.B.2 | 300-230 | 0.9 | 0.9 | 98.9 | 0.2 |

Figure 5:
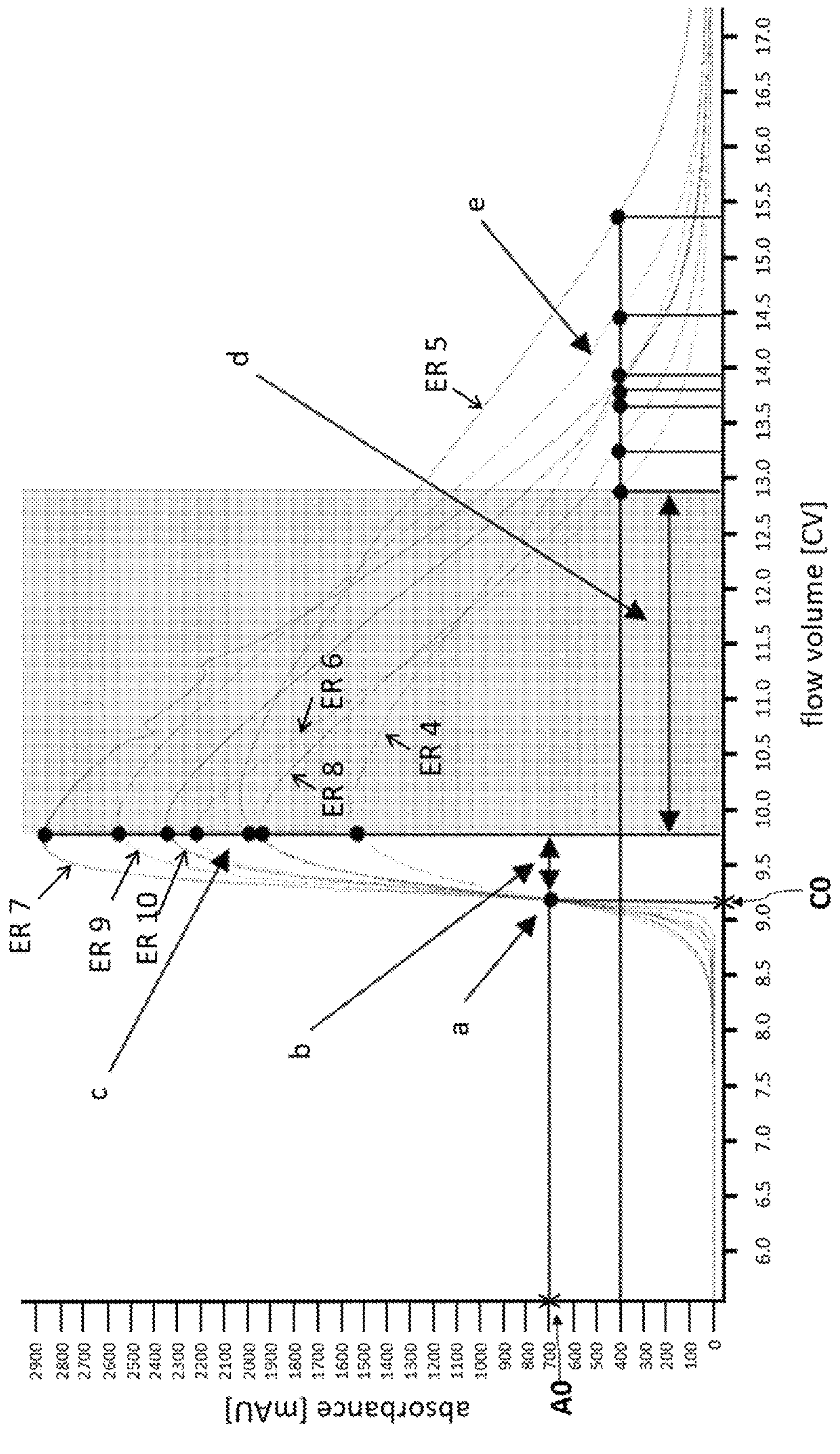
FIG. 5. Normalized elution peak chromatograms with peak collection start and end-points indicated for an antibody purification using Capto MMC ImpRes. The exemplified elution runs ($ER_4$ to $ER_{10}$) are under seven different conditions with varying pH and load density (Table 3) (a: intersection of A0 and normalized C0, b: predetermined D0 interval 'delay' (here: 0.6 CV); c: peak fractionation start (start of eluate collection); d: peak fractionation range, e: peak fractionation stop (stop of eluate collection) here at 400 mAU, UV 280 nm) A0: pre-determined absorbance signal, measured at UV 280 nm, here: 700 mAU).
Figure 6:
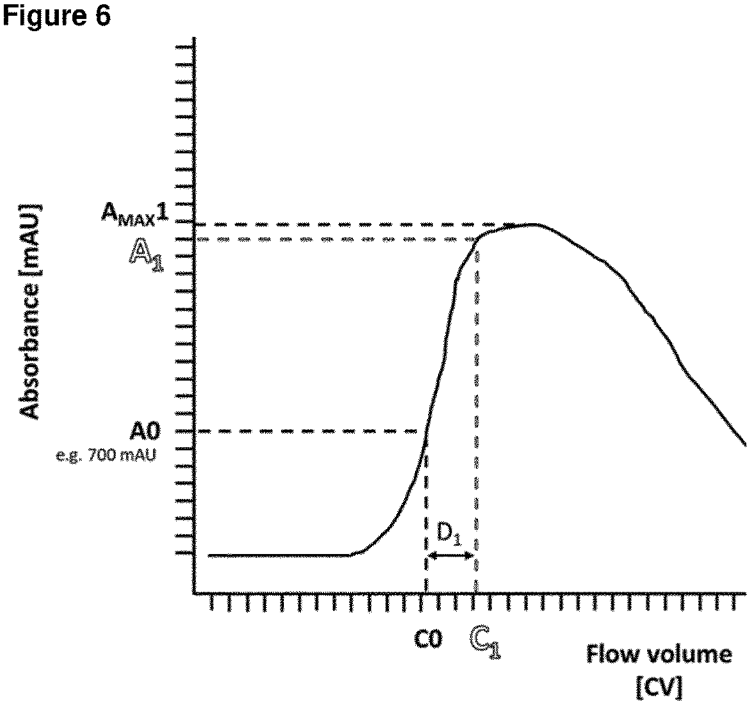
FIG. 6. Concept of determining the interval D0 to be used to reach the start point for eluate collection. Schematically exemplified are elution peaks of two elution runs with varying shape of the peaks. Reference absorbance A0 and the absorbance signals at maximum peak height ($A_{MAX}1$, $A_{MAX}2$) and for optimal elution start ($A_1$, $A_2$) and corresponding flow volumes C0, $C_1$ and $C_2$ are indicated. Optimal elution start relates to elution fractions with aggregate content and impurities within the specification. Typically, aggregates/impurities (i.e. HMW and LMW content) below 4% (i.e. monomer content above 96%) are considered optimal for the fractions.
Figure 6:
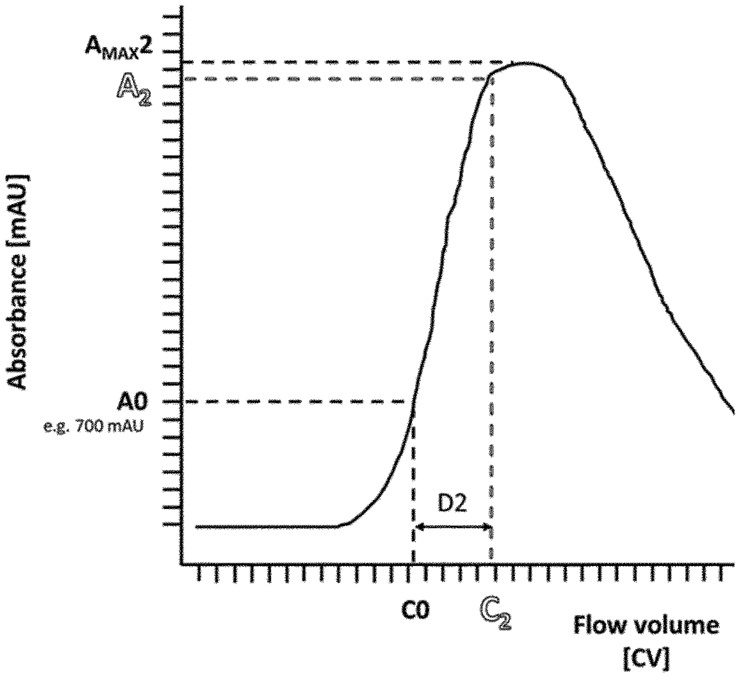
Figure 7:
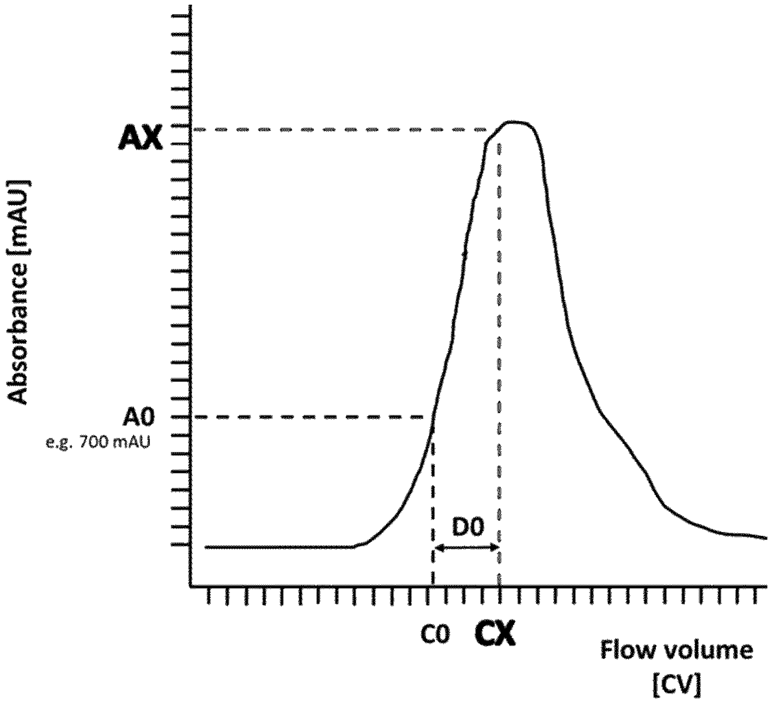
FIG. 7. Concept of applying the predetermined interval D0 on an elution peak with different shape (compared to the peak shapes exemplified in FIG. 5). Eluate collection starts at the flow volume interval D0 when CX is reached at absorbance signal AX.

Normalized elution peaks (according to flow volume) of different elution runs $ER_4$, . . . , $ER_{10}$ with eluate collection start at the predetermined interval are shown in FIG. 5. The endpoint for each eluate collection was set to 400 mAU. The yields and SEC monomer portions of the eluates obtained at the AX/D0 of the seven purification runs are summarized in Table 5.

TABLE 5

| Process parameters (pH, load amount) of seven purification runs $ER_4$ to $ER_{10}$ of an antibody on Capto MMC ImpRes and resulting yield and SEC monomer contents in the eluates collected at the predetermined interval D0. | | | | |
|---|---|---|---|---|
| Elution Run# | Gradient buffer pH | Load amount [g/L resin] | Yield [%] | SEC Monomer [%] |
| 4 | 5.35 | 20 | 72.5 | 99.2 |
| 5 | 5.35 | 32 | 81.6 | 99.0 |

TABLE 5-continued

| Process parameters (pH, load amount) of seven purification runs $ER_4$ to $ER_{10}$ of an antibody on Capto MMC ImpRes and resulting yield and SEC monomer contents in the eluates collected at the predetermined interval D0. | | | | |
|---|---|---|---|---|
| Elution Run# | Gradient buffer pH | Load amount [g/L resin] | Yield [%] | SEC Monomer [%] |
| 6 | 5.65 | 20 | 71.3 | 99.2 |
| 7 | 5.65 | 32 | 76.8 | 99.0 |
| 8 | 5.50 | 20 | 74.6 | 99.2 |
| 9 | 5.50 | 32 | 78.8 | 99.0 |
| 10 | 5.50 | 26 | 76.1 | 99.2 |

Example 3. Control Settings and Phase Properties

Figure 8:
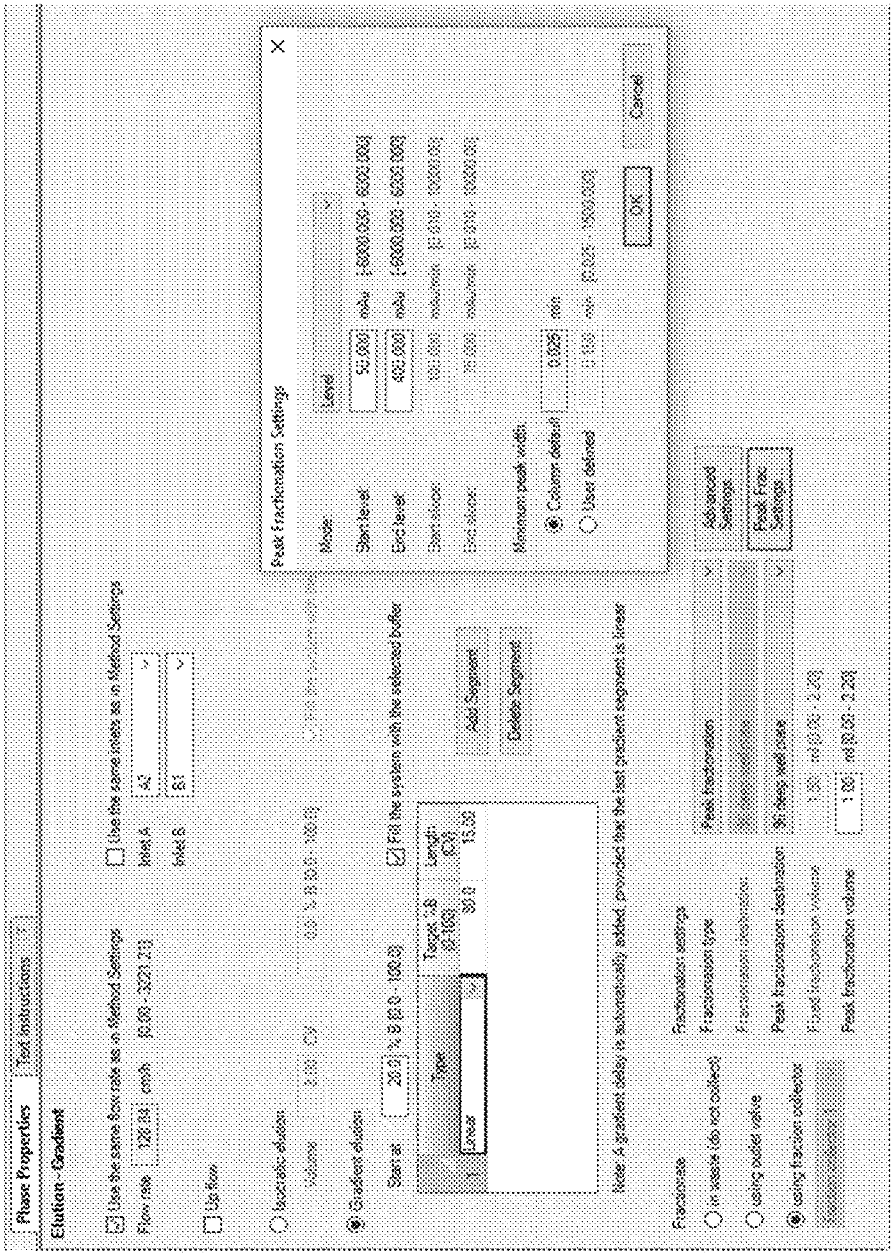
FIG. 8. Phase Properties of a predefined gradient elution phase within the Method Editor of UNICORN™ 7.1 (Build 7.1.0.378).

Within the Method Editor of the control software UNICORN™ 7.1 (Build 7.1.0.378, GE Healthcare) there is no possibility to integrate a 'delayed' peak fractionation start during linear gradient elution in the mask for the gradient elution phase (FIG. 8). Therefore, a computational command workaround was developed. The predefined elution phase of the UNICORN™ software was manually edited within the UNICORN™ Method Editor via text instructions, to set the desired 0.6 CV delayed peak fractionation start after a predefined, fix UV280 absorbance signal (here: 700 mAU). Therefore, fractionation start is independent of the maximum peak height. By this adaption of the predefined elution phase instructions within Unicorn, an optimal start of eluate collection was implemented, independent of process conditions and the resulting different elution peak shapes. Table 6 shows the text instructions of a standard predefined linear elution gradient phase in UNICORN™, with a peak fractionation start at 50 mAU. Table 7 shows the manually edited instructions of a linear elution gradient phase, with a 0.6 CV delayed peak fractionation start after a predetermined and pre-set UV280 absorbance signal of 700 mAU.

TABLE 6

Standard text instructions in UNICORN ™ 7.1 of a predefined linear elution gradient phase (see FIG. 8) with a fixed peak fractionation start at 50 mAU. Highlighted line in bold indicates the section for the fractionation start at a UV280 signal of 50 mAU.

0.00 Phase: Gradient
0.00 Base: SameAsMain
0.00 Inlet A: (A2)#Inlet A (Elution)
0.00 Inlet B: (B1)#Inlet B (Elution)
0.00 Gradient: (20.0)#Percent B (Elution) {%B}. 0.00 {base}
0.00 System flow: (128.84)#Flow rate {cm/h}. (Delta column pressure)#Pressure control
0.00 System wash: (15)#Fill system (Elution) {ml}. Injection valve
0.00 Block: Start frac (Elution)
0.00 Base: SameAsMain
0.00 Last tube filled: (Pause)#Last tube filled action (Elution)
0.00 Peak fractionation parameters: (Level)#Peak frac mode (Elution). (0.025)#Peak frac min peak width (Elution) {min}. (50.000)#Peak frac start level (Elution) {mAU}. (100.000)#Peak tract start slope (Elution) {mAU/min} . (25.000)#Peak frac end level (Elution)
0.00 Peak fractionation: Volume. (96 deep well plate)#Peak frac tube type (Elution). (1.00)#Peak frac volume (Elution) {ml}. (Next tube)#Peak frac start position (Elution)
0.00 End Block
0.00 Block: Linear gradient
0.00 Base: SameAsMain
0.00 Gradient: (80.0)#Gradient target (Elution) {%B}. (15.00)#Gradient length (Elution) {base}
15.00 End_Block
0.00 Block: Gradient delay
0.00 Block: Stop frac (Elution)
0.00 End_Block

TABLE 7

Manually edited text instruction entry into UNICORN ™ 7.1 for a linear elution gradient phase with a 0.6 CV delayed peak fractionation start after a predetermined UV280 signal of 700 mAU. Highlighted line in bold indicates the text instruction for fractionation start.

0.00 Phase: Elution Gradient
0.00 Base: SameAsMain
0.00 Inlet A: (A2)#Inlet A (Elution)_1
0.00 Inlet B: (B1)#inlet B (Elution)_1
0.00 Gradient: (20.0)#Percent B (Elution)_1 {%B}. 0.00 {base}
0.00 System flow: (150)#Flow rate (Elution)_1 {cm/h}. (Delta column pressure)#Pressure control
0.00 System wash: (15)#Fill system (Elution)_1 {ml}. Injection valve
0.00 Block: Start frac (Elution)_1
0.00 Base: SameAsMain
0.00 Last tube filled: (Pause)#Last tube filled action (Elution)_1
0.00 Fractionation: Volume. (15 ml tubes)#Frac tube type (Elution)_1. (7.0)#Frac volume (Elution)_1 {ml}. (Next tube)#Frac start position (Elution)_1
0.00 End_Block
0.00 Block:Linear gradient_1
0.00 Base: SameAsMain
0.00 Gradient: (80.0)#Gradient target (Elution)_1{%B}. (10.00)#Gradient length (Elution)_1 {base}
0.00 Watch: UV 1. Greater than.700.0 {mAU}.Collection
0.00 Base: SameAsMain
0.00 Watch: UV 1. Less than. 400.0 {mAU}. Stop frac (Elution)
0.00 Base: SameAsMain TABLE 7-continued

| Manually edited text instruction entry into UNICORN ™ 7.1 for a linear elution gradient phase with a 0.6 CV delayed peak fractionation start after a predetermined UV280 signal of 700 mAU. Highlighted line in bold indicates the text instruction for fractionation start. | |
|---|---|
| 0.00 | Stop peak fractionation |
| 0.00 | End_Block |
| 0.60 | Peak fractionation: Volume. (50 ml tubes)#Peak frac tube type (Elution)_1. (40.0)#Peak frac volume (Elution)_1 (ml). (Next tube)#Peak frac start position (Elution)_1 |
| 0.60 | End_Block |
| 10.00 | End_Block |
| 0.00 | Block: Gradient delay_1 |
| 0.00 | Block: Stop frac (Elution)_1 |
| 0.00 | End_Block |

The invention claimed is:

1. A method for the purification of an antibody by chromatography, comprising the following steps:

a) loading a sample comprising an antibody onto a chromatography resin, b) optionally, washing the resin, c) applying an elution buffer to the chromatography resin, and d) starting collection of the eluate, wherein the collection of the eluate is started at a predetermined interval (D0) after the absorbance signal of the eluate has reached a predetermined value (A0), and wherein the predetermined value (A0) is in the range of 10-50% of the absorbance signal at peak maximum of elution peaks obtained by different elution runs varying in pH conditions within a range of pH 5 to pH 7 and load density within a range of 5 to 50 g/l resin load with the antibody sample to be purified.

2. The method according to claim 1, wherein the predetermined absorbance value (A0) is in the range of 0 to 1500 mAU measured at 280 nm.

3. The method according to claim 2, wherein the predetermined absorbance value (A0) is 700 mAU measured at 280 nm.

4. The method according to claim 1, wherein the predetermined interval (D0) is a flow volume interval that is determined by the following steps:

a) receiving the elution peak chromatograms of at least two different elution runs ($ER_1, \ldots, ER_N$) with the antibody sample to be purified, wherein the different elution runs vary in pH, load density or salt conditions, b) specifying an absorbance signal $A_1, \ldots, A_N$ for each of the elution peaks received in step a), wherein each of the corresponding eluate fractions of $A_1, \ldots, A_N$ has an aggregate/impurity content below 4%, c) determining the flow volumes $C_1, \ldots, C_N$ of the absorbance signals $A_1, \ldots, A_N$ for each of the elution runs in the chromatograms, d) calculating the difference for each of said flow volumes $C_1, \ldots, C_N$, to the flow volume C0 of A0, and e) averaging said differences (i.e. obtaining the mean value), thereby obtaining the predetermined flow volume interval (D0).

5. The method according claim 4, wherein the distance of $A_1, \ldots, A_N$ to the absorbance signal $A_{MAX}$ at height maximum of the corresponding elution peak is in the range of 0 to 300 mAU measured at 280 nm.

6. The method according to claim 5, wherein the predetermined interval value (D0) is between 0.4 to 1.2 CV flow volumes.

7. The method according claim 6, wherein the predetermined interval value (D0) is 0.6 CV flow volumes.

8. The method according to claim 1, wherein the chromatography is ion exchange (IEX) chromatography.

9. The method according to claim 8, wherein the chromatography is cation exchange (CEX) chromatography.

10. The method according to claim 1, wherein the monoclonal antibody comprises a VH of SEQ ID NO: 8 and a VL of SEQ ID NO: 7.

11. The method according to claim 10, wherein the antibody comprises a heavy chain of SEQ ID NO: 10 and a light chain of SEQ ID NO: 9.

* * * * *

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 1

Asp Tyr Ala Met His
1 5

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 2

Tyr Ile Gly Gly Val Gly Glu Gly Thr Gln Tyr Ala Glu Ser Val Lys
1 5 10 15

Gly

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 3

Gly Phe Ala Ile Arg Tyr Tyr Gly Phe Asp Tyr
1 5 10

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 4

Ser Gly Asp Lys Leu Gly Asp Lys Tyr Ala Tyr
1 5 10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 5

Gln Asp Ser Lys Arg Pro Ser
1 5

<210> SEQ ID NO 6
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

Gln Val Phe Thr Phe Pro Leu Val Thr Thr
1 5 10

<210> SEQ ID NO 7
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

Ser Tyr Glu Leu Thr Gln Pro Pro Ser Val Ser Val Ser Pro Gly Gln
1 5 10 15

Thr Ala Ser Ile Thr Cys Ser Gly Asp Lys Leu Gly Asp Lys Tyr Ala
20 25 30

Tyr Trp Tyr Gln Gln Lys Pro Gly Gln Ser Pro Val Leu Val Ile Tyr
35 40 45

Gln Asp Ser Lys Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gln Val Phe Thr Phe Pro Leu Val Thr
85 90 95

Thr Val Phe Gly Gly Gly Thr Lys Leu Thr Val Leu Gly Gln
100 105 110

<210> SEQ ID NO 8
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Ala Met His Trp Val Arg Gln Ala Pro Gly Lys Gly Leu Glu Trp Val
        35                  40                  45

Ser Tyr Ile Gly Gly Val Gly Glu Gly Thr Gln Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Ala Ile Arg Tyr Tyr Gly Phe Asp Tyr Trp Gly Gln
            100                 105                 110

Gly Thr Leu Val Thr Val Ser Ser
        115                 120
```

<210> SEQ ID NO 9
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Val Phe Thr Phe Pro Leu Val Thr
                85                  90                  95

Thr Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 10
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Ala Met His Trp Val Arg Gln Ala Pro Gly Lys Gly Leu Glu Trp Val
        35                  40                  45

Ser Tyr Ile Gly Gly Val Gly Glu Gly Thr Gln Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Ala Ile Arg Tyr Tyr Gly Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 11
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

tcctacgagc tgacccagcc cccctccgtg tccgtgtctc ctggccagac cgcctccatc     60

acctgttccg gcgacaagct gggcgataag tacgcctact ggtatcagca gaagcccggc    120

cagtcccccg tgctggtcat ctaccaggac tccaagcggc cctccggcat ccctgagcgg    180

ttctccggct ccaactccgg caacaccgcc accctgacca tctccggcac ccaggccgag    240

gacgaggccg actactactg ccaggtgttc accttccccc tggtcaccac cgtgttcggc    300

ggaggcacca agctgaccgt gctgggccag                                     330


<210> SEQ ID NO 12
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12

gaggtgcagc tgctggaatc cggcggagga ctggtgcagc ctggcggctc cctgagactg     60

tcttgcgccg cctccggctt caccgtgtcc gactacgcta tgcactgggt ccgacaggcc    120

cctggcaagg gcctggaatg ggtgtcctat atcggcggcg tgggcgaggg cacccagtac    180

gctgagtctg tgaagggccg gttcaccatc tcccgggaca actccaagaa caccctgtac    240

ctgcagatga actccctgcg ggccgaggac accgccgtgt actactgtgc cagaggcttc    300

gccatccggt actacggctt cgactactgg ggccagggca ccctggtcac cgtgtctagc    360


<210> SEQ ID NO 13
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 13
tcctacgagc tgacccagcc cccctccgtg tccgtgtctc ctggccagac cgcctccatc 60
acctgttccg gcgacaagct gggcgataag tacgcctact ggtatcagca gaagcccggc 120
cagtcccccg tgctggtcat ctaccaggac tccaagcggc cctccggcat ccctgagcgg 180
ttctccggct ccaactccgg caacaccgcc accctgacca tctccggcac ccaggccgag 240
gacgaggccg actactactg ccaggtgttc accttccccc tggtcaccac cgtgttcggc 300
ggaggcacca agctgaccgt gctgggccag cctaaggccg ctccctccgt gaccctgttc 360
cccccatcct ccgaggaact gcaggccaac aaggccaccc tggtctgcct gatctccgac 420
ttctaccctg gcgccgtgac cgtggcctgg aaggccgaca gctctcctgt gaaggccggc 480
gtggaaacca ccacccccctc caagcagtcc aacaacaaat acgccgcctc ctcctacctg 540
tccctgaccc ccgagcagtg gaagtcccac cggtcctaca gctgccaggt cacacacgag 600
ggctccaccg tggaaaagac cgtggcccct accgagtgct cc 642

<210> SEQ ID NO 14
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14
gaggtgcagc tgctggaatc cggcggagga ctggtgcagc ctggcggctc cctgagactg 60
tcttgcgccg cctccggctt caccgtgtcc gactacgcta tgcactgggt ccgacaggcc 120
cctggcaagg gcctggaatg ggtgtcctat atcggcggcg tgggcgaggg cacccagtac 180
gctgagtctg tgaagggccg gttcaccatc tcccgggaca actccaagaa caccctgtac 240
ctgcagatga actccctgcg ggccgaggac accgccgtgt actactgtgc cagaggcttc 300
gccatccggt actacggctt cgactactgg ggccagggca ccctggtcac cgtgtctagc 360
gcctccacca agggcccctc cgtgttccct ctggcccccct ccagcaagtc cacctctggc 420
ggcaccgctg ccctgggctg cctggtcaag gactacttcc ccgagcccgt gaccgtgtcc 480
tggaactctg gcgccctgac ctccggcgtg cacaccttcc ctgccgtgct gcagtcctcc 540
ggcctgtact ccctgtcctc cgtcgtgacc gtgccctcca gctctctggg cacccagacc 600
tacatctgca acgtgaacca caagccctcc aacaccaagg tggacaagcg ggtggaaccc 660
aagtcctgcg acaagaccca cacctgtccc ccctgccctg cccctgaact gctgggcgga 720
ccttccgtgt tcctgttccc cccaaagccc aaggacaccc tgatgatctc ccggaccccc 780
gaagtgacct gcgtggtggt ggacgtgtcc cacgaggacc ctgaagtgaa gttcaattgg 840
tacgtggacg gcgtggaagt gcacaacgcc aagaccaagc ccagagagga acagtacaac 900
tccacctacc gggtggtgtc cgtgctgacc gtgctgcacc aggactggct gaacggcaaa 960
gagtacaagt gcaaggtgtc caacaaggcc ctgcctgccc ccatcgaaaa gaccatctcc 1020
aaggccaagg gccagccccg cgagccccag gtgtacacac tgccccctag ccgggaagag 1080
atgaccaaga accaggtgtc cctgacctgt ctggtcaagg gcttctaccc ctccgacatt 1140
gccgtggaat gggagtccaa cggccagccc gagaacaact acaagaccac cccccctgtg 1200
ctggactccg acggctcatt cttcctgtac tccaagctga ccgtggacaa gtcccggtgg 1260

-continued

```
cagcagggca acgtgttctc ctgctccgtg atgcacgagg ccctgcacaa ccactacacc   1320

cagaagtccc tgtccctgag ccccggcaag                                   1350
```